(12) United States Patent  
Aykroyd et al.

(10) Patent No.: US 9,965,587 B2  
(45) Date of Patent: May 8, 2018

(54) REMINDER, CLASSIFICATION, AND PATTERN IDENTIFICATION SYSTEMS AND METHODS FOR HANDHELD DIABETES MANAGEMENT DEVICES

(71) Applicant: Roche Diagnostics Operations, Inc., Indianapolis, IN (US)

(72) Inventors: Timothy N. Aykroyd, Carmel, IN (US); Amy C. Day, Fishers, IN (US); Paul J. Galley, Cumberland, IN (US); Horst Merkle, Indianapolis, IN (US); Christen A. Rees, Indianapolis, IN (US); Michelle M. Stevens, Fishers, IN (US); Scott A. Wooldridge, Carmel, IN (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 1219 days.

(21) Appl. No.: 13/936,534

(22) Filed: Jul. 8, 2013

(65) Prior Publication Data

US 2015/0012223 A1    Jan. 8, 2015

(51) Int. Cl.
*G01N 33/48* (2006.01)
*G06F 19/26* (2011.01)
*A61B 5/145* (2006.01)
*A61B 5/00* (2006.01)
*G06F 19/00* (2018.01)

(52) U.S. Cl.
CPC .......... *G06F 19/26* (2013.01); *A61B 5/14532* (2013.01); *A61B 5/7275* (2013.01); *G06F 19/345* (2013.01); *G06F 19/3456* (2013.01)

(58) Field of Classification Search
None
See application file for complete search history.

(56) References Cited

U.S. PATENT DOCUMENTS 7,976,467 B2    7/2011    Young et al.
8,066,640 B2 †  11/2011   Angelides
(Continued)

FOREIGN PATENT DOCUMENTS

EP    2103251    9/2009
EP    2384696    11/2011
(Continued)

*Primary Examiner* — Larry D Riggs, II
(74) *Attorney, Agent, or Firm* — Harness Dickey

(57) ABSTRACT

A method includes: measuring a blood glucose (bG) level in a blood sample; storing the bG level and a time of receipt of the blood sample; storing a classification of the blood sample; in response to the receipt of the blood sample, selecting a group of stored bG levels having the classification of the blood sample and that were received within a predetermined period before receipt of the blood sample; calculating a bG evaluation parameter from the selected bG levels; evaluating the bG evaluation parameter in relation to first predetermined criteria, the first predetermined criteria including a first threshold indicative of a high bG level or a low bG level; selectively displaying an indication of recognition of a pattern in the selected bG levels when the bG evaluation parameter is greater than or less than the first threshold; and selectively removing the indication from the display.

48 Claims, 11 Drawing Sheets

(56) References Cited

U.S. PATENT DOCUMENTS

| | | |
|---|---|---|
| 8,252,549 B2 | 10/2012 | Brauker et al. |
| 8,812,244 B2 † | 8/2014 | Angelides |
| 8,992,464 B2 * | 3/2015 | Bashan .............. A61B 5/14532 600/365 |
| 2004/0044272 A1 | 3/2004 | Moerman et al. |
| 2006/0010098 A1 † | 1/2006 | Angelides |
| 2007/0276197 A1 | 11/2007 | Harmon |
| 2008/0154513 A1 | 6/2008 | Kovatchev et al. |
| 2008/0234943 A1 | 9/2008 | Ray et al. |
| 2008/0234992 A1 | 9/2008 | Ray et al. |
| 2008/0235053 A1 | 9/2008 | Ray et al. |
| 2009/0149717 A1 | 6/2009 | Brauer et al. |
| 2009/0149729 A1 | 6/2009 | Young et al. |
| 2009/0237262 A1 | 9/2009 | Smith et al. |
| 2009/0240127 A1 | 9/2009 | Ray |
| 2010/0191075 A1 * | 7/2010 | Angelides .......... A61B 5/14532 600/301 |
| 2010/0312577 A1 | 12/2010 | Goodnow et al. |
| 2010/0331645 A1 * | 12/2010 | Simpson .............. A61B 5/0002 600/347 |
| 2010/0331654 A1 | 12/2010 | Jerdonek et al. |
| 2010/0332142 A1 | 12/2010 | Shadforth et al. |
| 2010/0332445 A1 | 12/2010 | Ray et al. |
| 2011/0040489 A1 | 2/2011 | Goodnow et al. |
| 2011/0040570 A1 | 2/2011 | Goodnow et al. |
| 2011/0046973 A1 | 2/2011 | Goodnow et al. |
| 2011/0046977 A1 | 2/2011 | Goodnow et al. |
| 2011/0071365 A1 | 3/2011 | Lee et al. |
| 2011/0092897 A1 | 4/2011 | Say et al. |
| 2011/0124996 A1 | 5/2011 | Reinke et al. |
| 2011/0178717 A1 | 7/2011 | Goodnow et al. |
| 2011/0184752 A1 | 7/2011 | Ray et al. |
| 2011/0205064 A1 | 8/2011 | Strachan et al. |
| 2011/0208027 A1 | 8/2011 | Wagner et al. |
| 2011/0263959 A1 | 10/2011 | Young et al. |
| 2011/0270063 A1 | 11/2011 | Young et al. |
| 2012/0130646 A1 | 5/2012 | Landis et al. |
| 2013/0035563 A1 * | 2/2013 | Angelides .......... A61B 5/14532 600/301 |
| 2013/0338453 A1 | 12/2013 | Duke et al. |

FOREIGN PATENT DOCUMENTS

| | | |
|---|---|---|
| EP | 2455875 | 5/2012 |
| EP | 2455876 | 5/2012 |
| EP | 2455877 | 5/2012 |
| EP | 2537467 A1 | 12/2012 |
| WO | WO2006/072035 | 7/2003 |
| WO | WO2009/075697 | 6/2009 |
| WO | WO-2009071202 A2 | 6/2009 |
| WO | WO2011/002791 | 1/2011 |

\* cited by examiner
† cited by third party

Timing Data — 544

| Object/Attribute | |
|---|---|
| Waking Time | 604 |
| Breakfast Time | 608 |
| Lunch Time | 612 |
| Dinner Time | 616 |
| Bed Time | 620 |
| Post-Meal Period | 624 |
| Hypo Followup Period | 628 |

FIG. 6

Reminder Data — 548

| Object/Attribute | |
|---|---|
| Waking Enable/Disable | 704 |
| Breakfast Enable/Disable | 708 |
| Lunch Enable/Disable | 712 |
| Dinner Enable/Disable | 716 |
| Bed Enable/Disable | 720 |
| Post-Meal Enable/Disable | 724 |
| Hypo Followup Enable/Disable | 728 |

FIG. 7

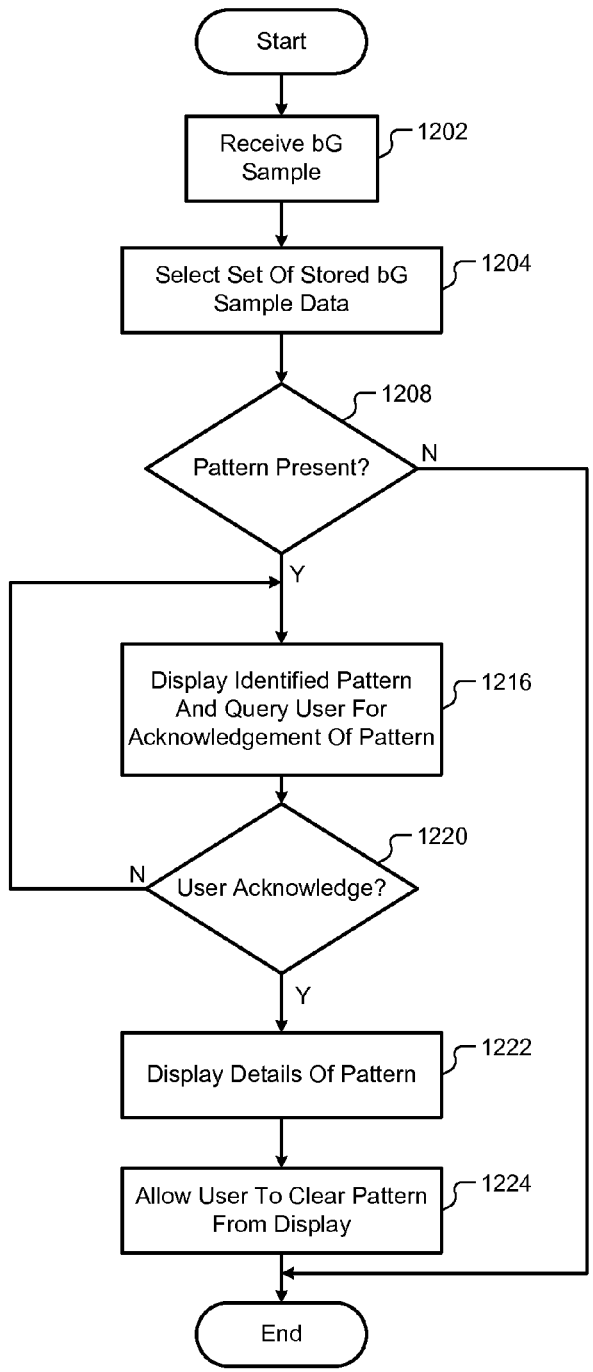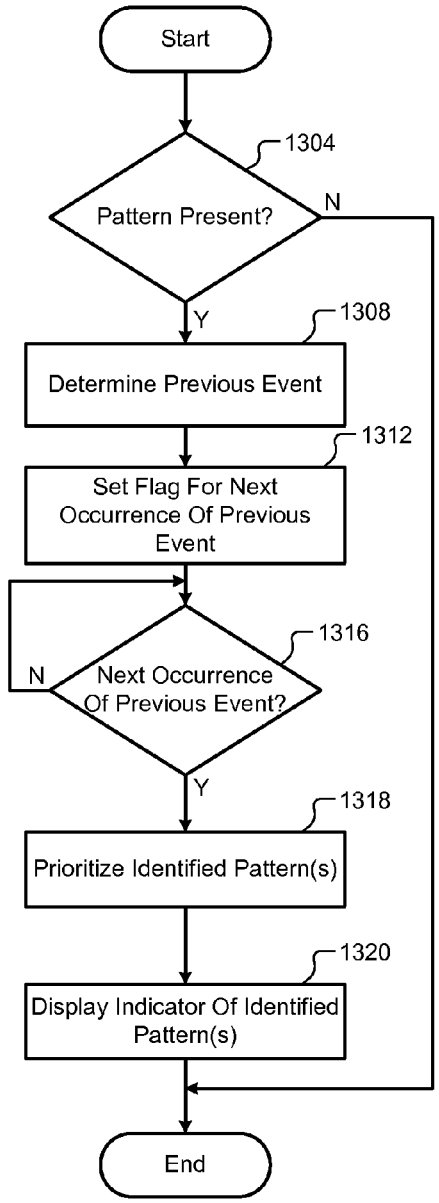
FIG. 12
FIG. 13

REMINDER, CLASSIFICATION, AND PATTERN IDENTIFICATION SYSTEMS AND METHODS FOR HANDHELD DIABETES MANAGEMENT DEVICES

FIELD

The present disclosure relates to handheld medical devices and more particularly to systems and methods for reminding users to take blood glucose (bG) measurements, identifying types of bG measurements, and identifying trends in bG measurements using a handheld bG measurement device.

BACKGROUND

Persons with diabetes have difficulty regulating blood glucose levels in their bodies. As a consequence, many of these persons carry specialized electronic meters, called blood glucose meters, which allow them to periodically measure their glucose levels and take appropriate action, such as administering insulin. These persons may also carry with them a portable communication device, such as a mobile phone, a personal digital assistant, a tablet or similar device. People often rely on their portable communication device as the primary means for planning, scheduling and communicating with others. As a result, most portable communication devices are equipped with sophisticated software which provides user-friendly means for viewings and inputting data.

User interfaces of handheld diabetes management devices, including blood glucose meters, may be limited to limit the complication associated with operating the diabetes management device. There is a need for handheld diabetes management devices that, while having limited user interfaces, have easily user-configurable reminders for taking blood glucose (bG) measurements, automatically classify bG measurements as a specific type of bG measurement, and identify and notify a user of trends in stored bG measurements, for example, based on classification.

The background description provided herein is for the purpose of generally presenting the context of the disclosure. Work of the presently named inventors, to the extent it is described in this background section, as well as aspects of the description that cannot otherwise qualify as prior art at the time of filing, are neither expressly nor impliedly admitted as prior art against the present disclosure.

SUMMARY

In a feature, a handheld diabetes management device for classifying blood samples and identifying medically relevant patterns in groups of blood samples is disclosed. The handheld diabetes management device includes: a blood glucose (bG) measurement engine that measures bG levels in blood samples input to the handheld diabetes management device; a display; a clock tracking a present date and time; a processor; and memory including code executed by the processor. The code is for: measuring a blood glucose (bG) level in a blood sample received by the handheld diabetes management device; storing the bG level and a time of receipt of the blood sample in memory; storing a classification of the blood sample, wherein the classification is one of a fasting sample, a pre-breakfast sample, a post-breakfast sample, a pre-lunch sample, a post-lunch sample, a pre-dinner sample, a post-dinner sample, and a bed time sample; selecting a group of stored bG levels having one of the classifications; and generating an indicator of recognition of a pattern in the selected group of bG levels when a bG evaluation parameter calculated based on the selected bG levels is one of greater than a first threshold indicative of a high bG level and less than a second threshold indicative of a low bG level. The code is further for, in response to a user request to display recognized patterns in bG levels: generating a list of recognized patterns including the pattern in the selected bG levels; prioritizing the list based on predetermined prioritization criteria; and displaying the list on a display.

In a feature, a method for classifying blood samples and identifying medically relevant patterns in groups of blood samples is disclosed. The method includes: measuring a blood glucose (bG) level in a blood sample received by a handheld diabetes management device; storing the bG level and a time of receipt of the blood sample in memory; storing a classification of the blood sample, wherein the classification is one of a fasting sample, a pre-breakfast sample, a post-breakfast sample, a pre-lunch sample, a post-lunch sample, a pre-dinner sample, a post-dinner sample, and a bed time sample; selecting a group of stored bG levels having one of the classifications; and generating an indicator of recognition of a pattern in the selected group of bG levels when a bG evaluation parameter calculated based on the selected bG levels is one of greater than a first threshold indicative of a high bG level and less than a second threshold indicative of a low bG level. The method further includes, in response to a user request to display recognized patterns in bG levels: generating a list of recognized patterns including the pattern in the selected bG levels; prioritizing the list based on predetermined prioritization criteria; and displaying the list on a display.

In a feature, a handheld diabetes management device for classifying blood samples and identifying medically relevant patterns in groups of blood samples is disclosed. The handheld diabetes management includes: a blood glucose (bG) measurement engine that measures bG levels in blood samples input to the handheld diabetes management device; a display; a clock tracking a present date and time; a processor; and memory including code executed by the processor. The code is for: storing the bG level and a time of receipt of the blood sample in memory; storing a classification of the blood sample, wherein the classification is one of a fasting sample, a pre-breakfast sample, a post-breakfast sample, a pre-lunch sample, a post-lunch sample, a pre-dinner sample, a post-dinner sample, and a bed time sample; in response to the receipt of the blood sample, selecting a group of stored bG levels having the classification of the blood sample and that were received within a predetermined period before receipt of the blood sample; calculating a bG evaluation parameter from the selected bG levels; evaluating the bG evaluation parameter in relation to first predetermined criteria, the first predetermined criteria including a first threshold indicative of a high bG level or a low bG level; and selectively displaying an indication of recognition of a pattern in the selected bG levels when the bG evaluation parameter is greater than or less than the first threshold.

In a feature, a method for classifying blood samples and identifying medically relevant patterns in groups of blood samples is disclosed. The method includes: measuring a blood glucose (bG) level in a blood sample received by a handheld diabetes management device; storing the bG level and a time of receipt of the blood sample in memory; storing a classification of the blood sample, wherein the classification is one of a fasting sample, a pre-breakfast sample, a post-breakfast sample, a pre-lunch sample, a post-lunch sample, a pre-dinner sample, a post-dinner sample, and a bed time sample; and in response to the receipt of the blood sample, selecting a group of stored bG levels having the classification of the blood sample and that were received within a predetermined period before receipt of the blood sample. The method further includes: calculating a bG evaluation parameter from the selected bG levels; evaluating the bG evaluation parameter in relation to first predetermined criteria, the first predetermined criteria including a first threshold indicative of a high bG level or a low bG level; selectively displaying an indication of recognition of a pattern in the selected bG levels when the bG evaluation parameter is greater than or less than the first threshold; and removing the indication from the display only in response to receipt of predetermined user input indicative of an acknowledgement of the presence of the pattern.

Further areas of applicability of the present disclosure will become apparent from the detailed description provided hereinafter. It should be understood that the detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings, wherein:

FIGS. 6-7 include example illustrations of various data stored in memory;

FIG. 12 includes a flowchart depicting an example method of identifying and displaying patterns in bG sample data;

FIG. 13 includes a flowchart depicting an example method of, based on recognition of a pattern associated with a daily event, displaying a reminder of the presence of the pattern at an event before that event.

DETAILED DESCRIPTION

Figure 1:
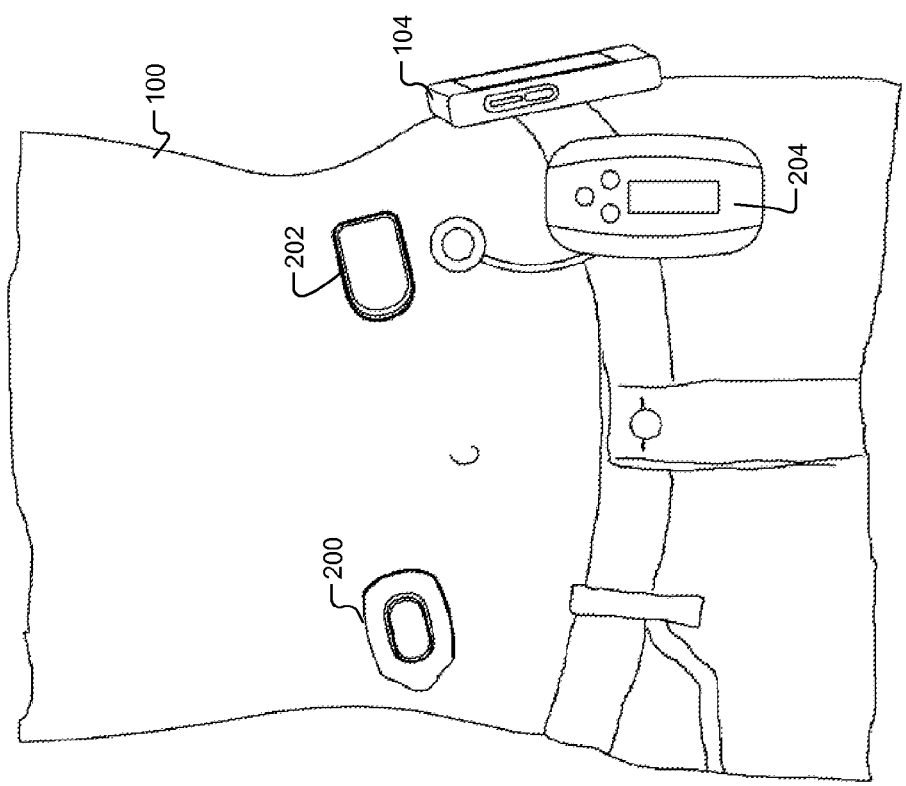
FIG. 1 shows a patient and a health care professional along with various devices that can be used to help the patient monitor and control health.

Referring now to FIG. 1, a patient 100 with diabetes and a health care professional 102 are shown in a clinical environment. The patient 100 with diabetes can be diagnosed with a metabolic syndrome, pre-diabetes, type 1 diabetes, type 2 diabetes, gestational diabetes, etc. Healthcare providers for diabetes are diverse and include nurses, nurse practitioners, physicians, endocrinologists, and others and are collectively referred to as health care professionals.

During a health care consultation, the patient 100 typically shares with the health care professional 102 a variety of data including blood glucose (bG) measurements, continuous glucose monitor data, amounts and type of insulin administered, amounts of food and beverages consumed, exercise schedules, health status, and other lifestyle information. The health care professional 102 can obtain additional data for the patient 100, such as measurements of HbA1C, cholesterol levels, plasma glucose, triglycerides, blood pressure, and weight. The data can be recorded manually or electronically on a handheld diabetes management device 104 (e.g., a handheld bG monitor device), diabetes analysis software executed on a personal computer (PC) 106, and/or a web-based diabetes analysis site. The health care professional 102 can analyze the patient data manually or electronically using the diabetes analysis software and/or the web-based diabetes analysis site. After analyzing the data and reviewing how efficacious previously prescribed therapy is and how well the patient 100 followed the previously prescribed therapy, the health care professional 102 can decide whether to modify a therapy prescribed for the patient 100.

Figure 2:
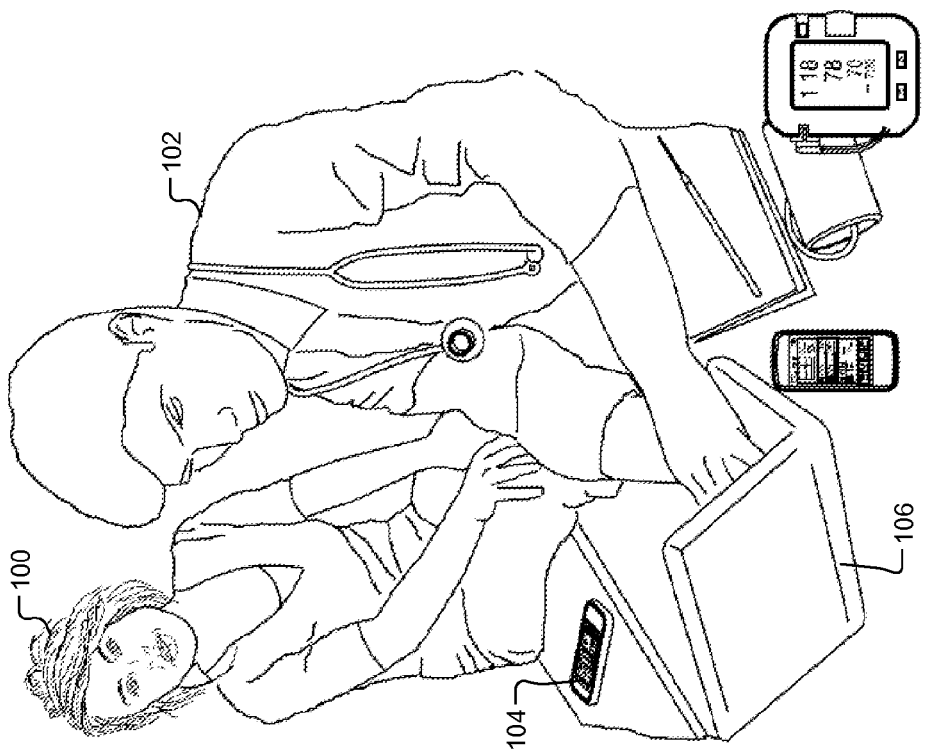
FIG. 2 shows a patient with a continuous glucose monitor (CGM), an ambulatory durable insulin infusion pump, an ambulatory non-durable insulin infusion pump, and a blood glucose (bG) management device.

Referring now to FIG. 2, the patient 100 can use a continuous glucose monitor (CGM) 200, an ambulatory durable insulin infusion pump 204 or an ambulatory non-durable insulin infusion pump 202 (collectively insulin pump 204), and the diabetes management device 104. The CGM 200 can use a subcutaneous sensor to sense and monitor the amount of glucose (e.g., glucose concentration) of the patient 100. The CGM 200 communicates glucose measurements to the diabetes management device 104.

The diabetes management device 104 performs various tasks including measuring and recording bG measurements, determining an amount of insulin to be administered to the patient 100 via the insulin pump 204, receiving user input via a user interface, archiving data, performing structured bG tests, etc. The diabetes management device 104 can transmit instructions to the insulin pump 204, and the insulin pump 204 selectively delivers insulin to the patient 100. Insulin can be delivered in the form of a meal bolus dose, a correction bolus dose, a basal dose, etc.

Figure 3:
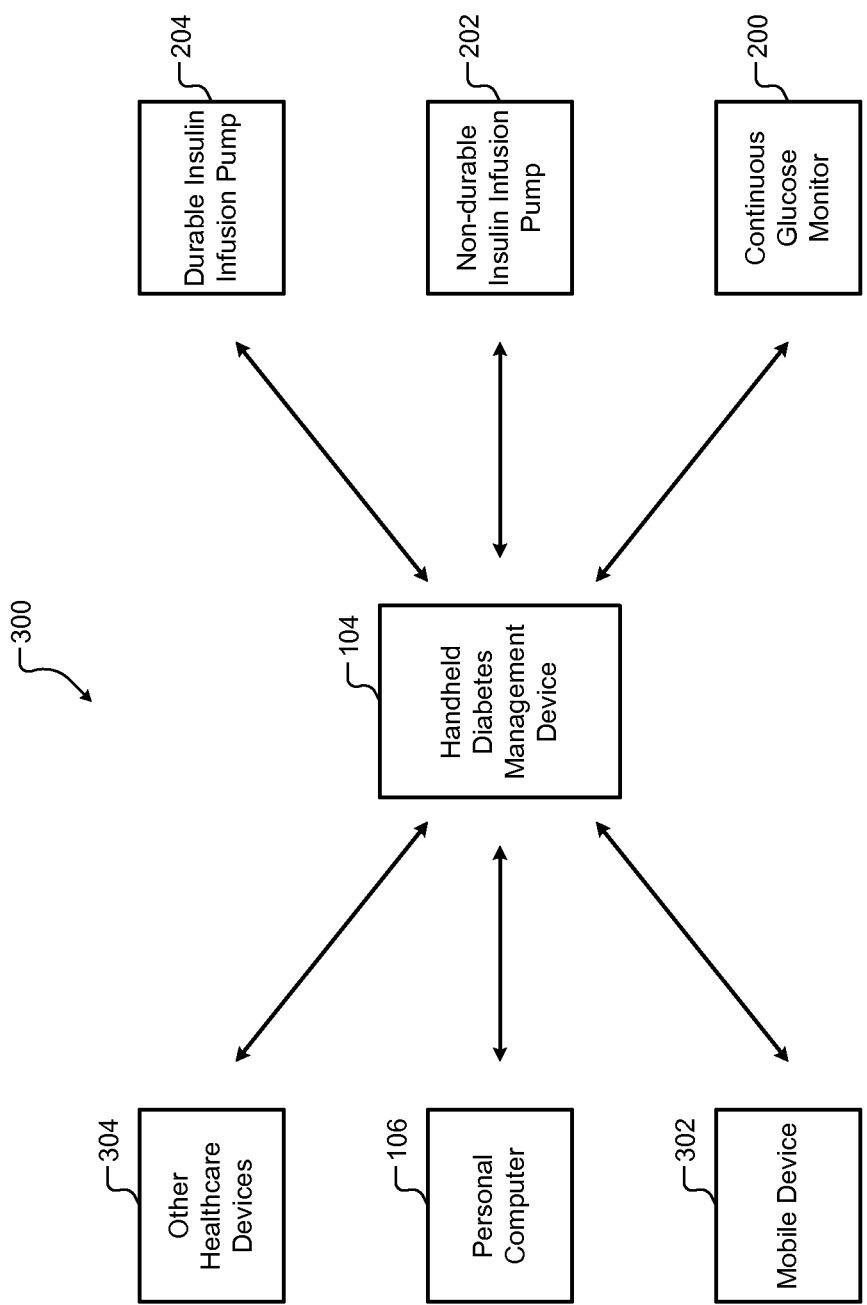
FIG. 3 shows a diabetes care system of systems that can be used to manage diabetes.

Referring now to FIG. 3, a diabetes management system 300 is shown which can be used by the patient 100 and/or the health care professional 102. The system 300 can include one or more of the following devices: the diabetes management device 104, the CGM 200, the insulin pump 204, a mobile device 302, the diabetes management software executed on the computer 106, and one or more other health care devices 304.

The diabetes management device 104 can be configured as a system "hub" and communicate with one or more of the other devices of the system 300. The insulin pump 204, the mobile device 302, or another suitable device can alternatively serve as the system hub. Communication between various devices in the system 300 can be performed using wireless interfaces (e.g., Bluetooth) and/or wired interfaces (e.g., USB). Communication protocols used by these devices can include protocols compliant with the IEEE 11073 standard as extended using guidelines provided by Continua Health Alliance Design Guidelines. Further, health care records systems such as Microsoft HealthVault™ and Google Health™ can be used by the patient 100 and the health care professional 102 to exchange information.

Figure 4:
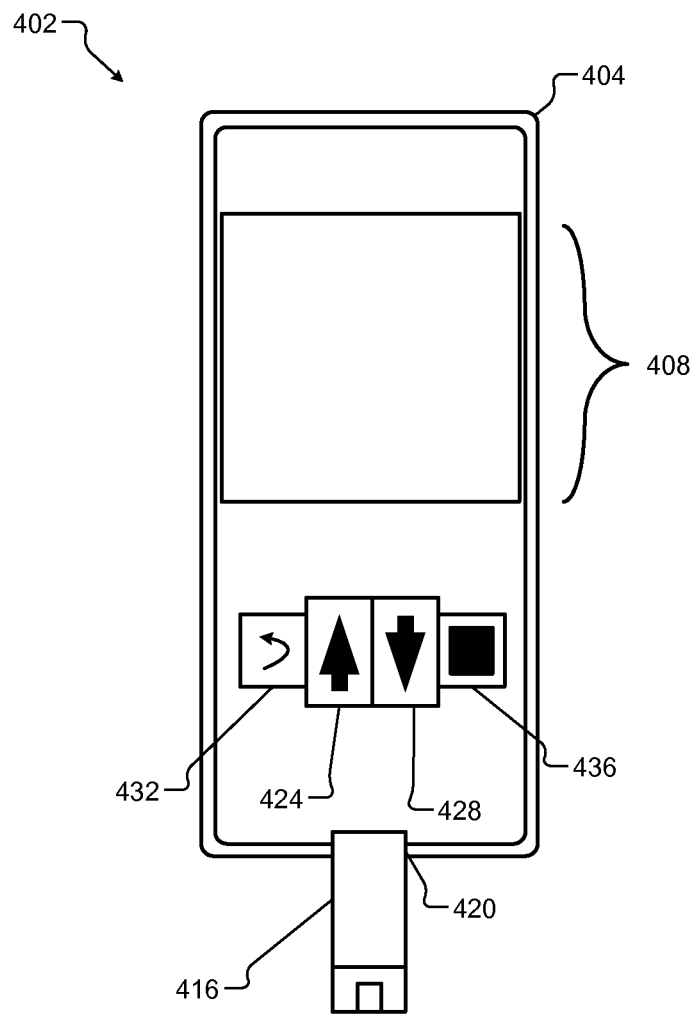
FIG. 4 is a high level diagram of an example implementation of a diabetes management device.

Referring now to FIG. 4, a high level illustration of an example embodiment of a (handheld) diabetes management device 402 is presented. The diabetes management device 402 includes, among other things, a housing 404, a display 408, and a bG test strip port 420. The diabetes management module 402 may optionally include a bG test strip drum (not shown). The bG test strip drum may house a plurality of bG test strips, such as bG test strip 416.

The diabetes management device 402 also includes user interface switches/buttons, such as up button 424, down button 428, back button 432, and enter button 436. The user interface switches/buttons can also include other buttons or switches, for example, ON/OFF switches and/or one or more other switches/buttons or other types of control devices that a patient can use to control functions/operations of the diabetes management device 402.

The bG test strip 416 can be inserted into the bG test strip port 420 by a user. The bG test strip 416 is shown already inserted into the bG test strip port 420 in the example of FIG. 4 and not yet inserted into the bG test strip port 420 in the example of FIG. 5. The display 408 of the diabetes management device 402 may be a non-touch screen display, such as a dot-matrix display. Various information may be selectively displayed on the display 408. For example, a bG measurement may be displayed on the display 408 when a bG measurement is made in response to insertion of a bG test strip.

Figure 5:
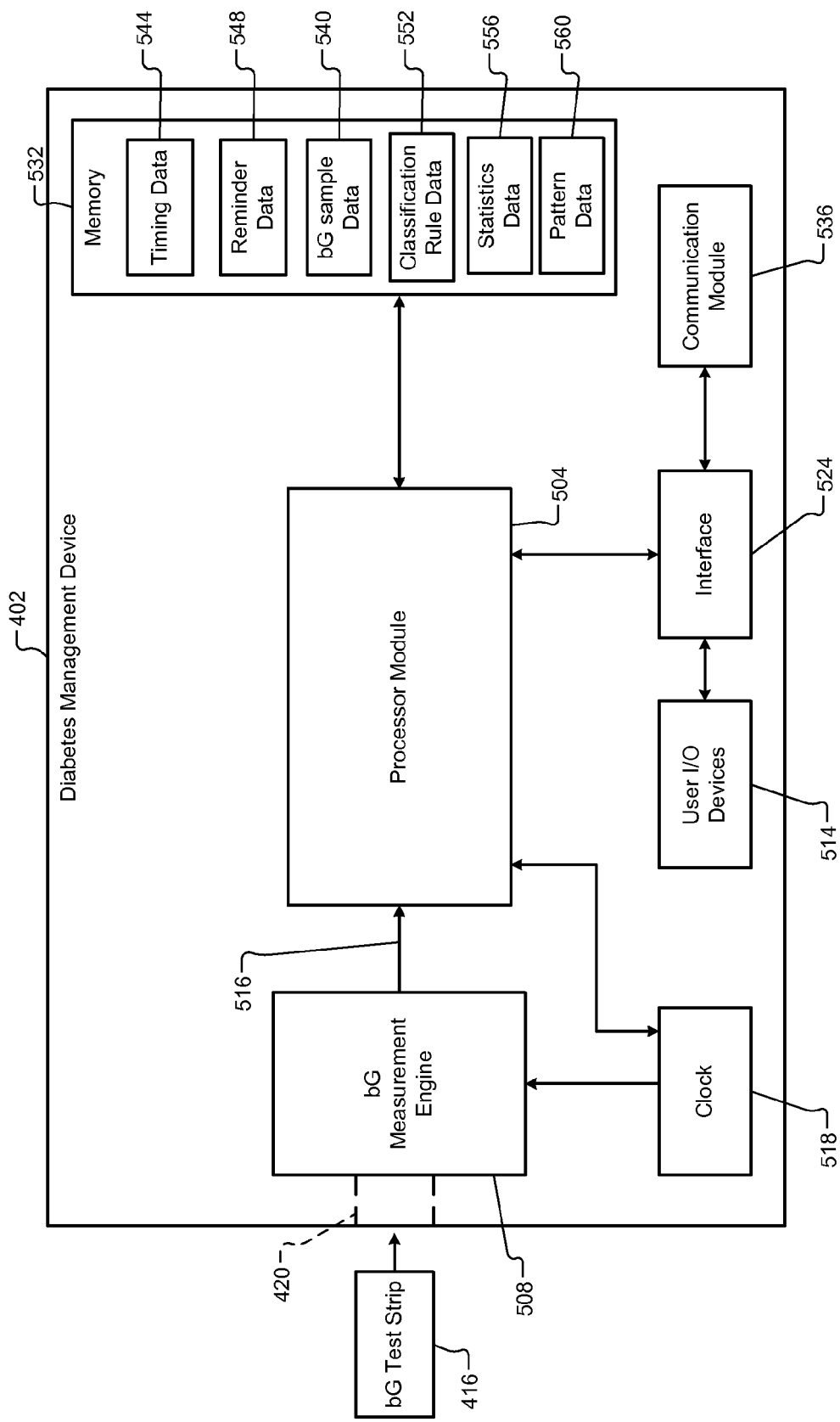
FIG. 5 includes a functional block diagram of an example implementation of a diabetes management device.

Referring now to FIG. 5, a functional block diagram of an example implementation of the diabetes management device 402 is presented. The diabetes management device 402 includes a processor module (e.g., a microprocessor based subsystem) 504 that can receive information from a bG measurement engine 508.

The bG measurement engine 508 reads (measures) bG levels of blood samples present on bG test strips inserted into the bG test strip port 420. For example, the bG measurement engine 508 measures a bG level of the bG test strip 416 when inserted into the bG test strip port 420. The bG measurement engine 508 can be located adjacent the bG test strip port 420. The bG measurement engine 508 generates bG sample data 516 based on its reading of a blood sample present on a bG test strip. Among other things, the bG sample data 516 includes data indicative of the bG level of a bodily fluid sample on the bG test strip.

The bG measurement engine 508 can also generate the bG sample data 516 to include the date and time when the bG test strip 416 was read. In other words, the bG measurement engine 508 can include a time stamp with the bG sample data 516. In various implementations, the processor module 504 can selectively time stamp the bG sample data 516. A clock 518 may track the present day, date, and time. Time stamps may include data indicative of the date and time and may also include the day.

The processor module 504 can receive user input and output information to a user via one or more user input/output (I/O) devices 514, such as the buttons 424-436 and the display 408. One or more I/O interfaces, such as I/O interface 524, facilitate communication between the user I/O devices 514 and the processor module 504. The I/O interfaces may also facilitate communication between the processor module 504 and one or more communication modules, such as communication module 536. The communication module 536 may include a wireless transceiver and communicate (transmit and receive) wirelessly via one or more antennas.

The diabetes management device 402 includes a tangible computer-readable medium, such as memory and/or one or more other suitable tangible, computer readable mediums. Various data may be stored in the memory 532, such as bG sample data 540 and other types of data, as discussed further below. The bG sample data 540 may include bG sample data generated by the bG measurement engine 508, such as the bG sample data 516. The bG sample data 540 may also include other types of data related to bG samples.

bG measurements provided regularly at approximately the same time(s) and/or around the same daily event(s) yield better results in terms of bG management than bG measurements provided randomly. For example, a bG management strategy generated based on bG measurements provided at the same daily event(s) may be more accurate than a bG management strategy generated based on various bG measurements taken under different conditions on various days. This is because a user's bG level constantly changes and changes with food intake, exercise, stress, etc. Measurements taken at or around the same daily event(s) can be used to provide better suggestions as to what actions to take before and after those daily event(s).

Timing data 544 includes times for daily events and times/periods for other events. FIG. 6 includes an example illustration of contents of the timing data 544. Referring now to FIGS. 5 and 6, the daily events may include, for example, waking up/rising, breakfast, lunch, dinner, and bed. The timing data 544 therefore includes data indicative of a waking time 604 for waking up/rising, a breakfast time 608 for breakfast, a lunch time 612 for lunch, a dinner time 616 for dinner, and a bed time 620 for bed time.

The other events may include, for example, post-meal bG measurements and hypoglycemic followup bG measurements. The timing data 544 therefore includes data indicative of a post-meal period 624 for post-meal bG measurements and a hypo followup period 628 for hypoglycemic followup bG measurements. In various implementations, the timing data 544 may include a post-meal period for breakfast, a post-meal period for lunch, and a post-meal period for dinner. A bG measurement may be deemed hypoglycemic when its bG level is less than a predetermined hypoglycemic bG value. A hypoglycemic followup bG measurement may refer to a measurement taken following a bG measurement deemed hypoglycemic.

The waking time 604, the breakfast time 608, the lunch time 612, the dinner time 616, the bed time 620, the post-meal period 624, and the hypo followup period 628 are predetermined values and may be set, for example, by a manufacturer of the diabetes management device 402. For example only, the waking time 604 may be set to approximately 7:00 am, the breakfast time 608 may be set to approximately 8:00 am, the lunch time 612 may be set to approximately 12:00 pm, the dinner time 616 may be set to approximately 5:00 pm, the bed time 620 may be set to approximately 9:00 pm, the post-meal period 624 may be set to approximately 2 hours, and the hypo followup period 628 may be set to approximately 15 minutes.

The waking time 604, the breakfast time 608, the lunch time 612, the dinner time 616, the bed time 620, the post-meal period 624, and/or the hypo followup period 628 can be adjusted by a user, such as via one or more of the buttons 424-436. The waking time 604, the breakfast time 608, the lunch time 612, the dinner time 616, the bed time 620, the post-meal period 624, and/or the hypo followup period 628 may be adjusted, for example, to more accurately reflect when those events take place in the user's daily life.

The diabetes management device 402 may remind the user to input a bG measurement for one or more of the events. For example only, the processor module 504 may display a reminder on to input a bG measurement on the display 408 and/or generate one or more other alerts (e.g., audible, visual, and/or tactile) to remind the user to input a bG measurement for an event.

Reminder data 548 includes data indicating whether to remind the user for each of the events. FIG. 7 includes an example illustration of contents of the reminder data 548. Referring now to FIGS. 5-7, the reminder data 548 includes waking enable/disable data 704 that is associated with/ related to the waking time 604. The waking enable/disable data 704 indicates whether to remind the user to input a bG measurement at the waking time 604.

The reminder data 548 also includes breakfast enable/ disable data 708 that is associated with/related to the breakfast time 608. The breakfast enable/disable data 708 indicates whether to remind the user to input a bG measurement at the breakfast time 608, before consuming breakfast. Lunch enable/disable data 712 is associated with/related to the lunch time 612. The lunch enable/disable data 712 indicates whether to remind the user to input a bG measurement at the lunch time 612, before consuming lunch. Dinner enable/disable data 716 is associated with/related to the dinner time 616. The dinner enable/disable data 716 indicates whether to remind the user to input a bG measurement at the dinner time 616, before consuming dinner. Bed enable/disable data 720 is associated with/related to the bed time 620. The bed enable/disable data 720 indicates whether to remind the user to input a bG measurement at the bed time 620.

Post-meal enable/disable data 724 is associated with/ related to the post-meal period 624. The post-meal enable/ disable data 724 indicates whether to remind the user to input a bG measurement the post-meal period 624 after a bG measurement is received for (or the time associated with) a given meal, such as breakfast, lunch, or dinner. Hypo followup enable/disable data 728 is associated with/related to the hypo followup period 628. The hypo followup enable/ disable data 728 indicates whether to remind the user to input a bG measurement the hypo followup period 628 after a bG measurement is received that is deemed hypoglycemic.

The waking enable/disable data 704, the breakfast enable/ disable data 708, the lunch enable/disable data 712, the dinner enable/disable data 716, bed enable/disable data 720, the post-meal enable/disable data 724, and the hypo followup enable/disable data 728 are predetermined values and may be set, for example, by the manufacturer of the diabetes management device 402. However, the waking enable/disable data 704, the breakfast enable/disable data 708, the lunch enable/disable data 712, the dinner enable/disable data 716, bed enable/disable data 720, the post-meal enable/ disable data 724, and the hypo followup enable/disable data 728 can be adjusted by a user, such as via one or more of the buttons 424-436.

The waking enable/disable data 704, the breakfast enable/ disable data 708, the lunch enable/disable data 712, the dinner enable/disable data 716, the bed enable/disable data 720, the post-meal enable/disable data 724, and the hypo followup enable/disable data 728 may each include other data. For example, a time stamp may be included when that piece of enable/disable data was set to disable generation of the associated reminder.

The processor module 504 selectively generates reminders to input a bG measurement for the events at the associated times (as indicated in the timing data 544) based on whether reminders for the events are enabled or disabled (as indicated in the reminder data 548), respectively. For example, when the waking enable/disable data 704 is set to enable waking reminders, the processor module 504 generates a reminder to provide a bG measurement at the waking time 604.

When the breakfast enable/disable data 708 is set to enable breakfast reminders, the processor module 504 generates a reminder to provide a bG measurement at the breakfast time 608. When the lunch enable/disable data 712 is set to enable lunch reminders, the processor module 504 generates a reminder to provide a bG measurement at the lunch time 612. When the dinner enable/disable data 716 is set to enable dinner reminders, the processor module 504 generates a reminder to provide a bG measurement at the dinner time 616. When the bed enable/disable data 720 is set to enable bed reminders, the processor module 504 generates a reminder to provide a bG measurement at the bed time 620.

When the post-meal enable/disable data 724 is set to enable post-meal reminders, the processor module 504 generates a reminder to provide a bG measurement the post-meal period 624 after the one of the times 608-616 for that meal or the post-meal period after receipt of a bG measurement for that meal. When the hypo followup enable/disable data 728 is set to enable reminders following hypoglycemic bG measurements, the processor module 504 generates a reminder to provide a bG measurement the hypo followup period 628 after receipt of a hypoglycemic bG measurement. As described above, the reminder may include, for example, a reminder to input a bG measurement displayed on the display 408 and/or one or more other alerts (e.g., audible, visual, and/or tactile) to remind the user to input a bG measurement.

Figure 8:
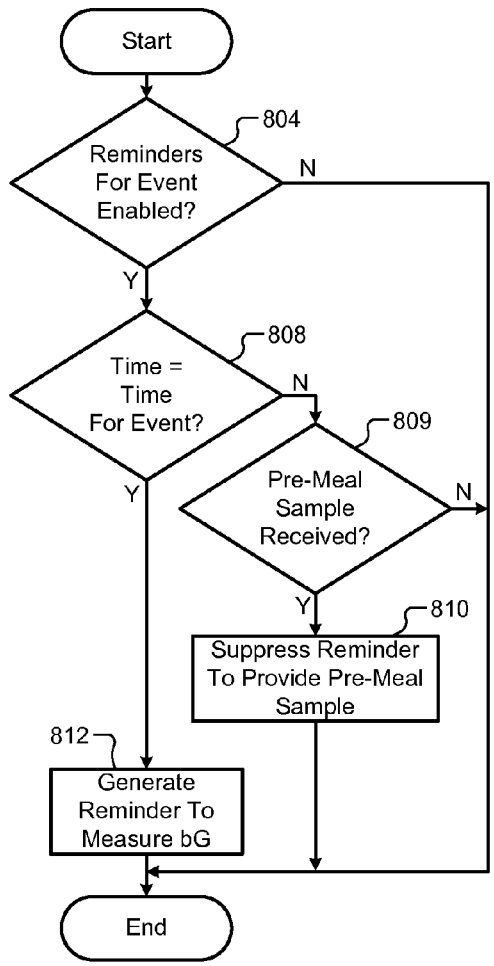
FIG. 8 includes a flowchart depicting an example method of generating a reminder to measure bG for an event.

FIG. 8 is a flowchart depicting an example method of generating a reminder to measure bG for an event. While the event will be discussed as waking, FIG. 8 is also applicable to generating a reminder to measure bG for other events, such as for breakfast, lunch, dinner, and bed. At 804, the processor module 504 may determine whether reminders for waking are enabled. The processor module 504 may determine whether reminders for waking are enabled based on the waking enable/disable data 704. If 804 is true, control may continue with 808. If 804 is false, control may end.

At 808, the processor module 504 retrieves the waking time 604 and the present time, and the processor module 504 determines whether the present time is the same as the waking time 604. If 808 is false, control may continue with 809. If 808 is true, the processor module 504 generates a reminder to measure bG level at 812, and control may end. As discussed above, the reminder may include, for example, displaying a reminder to measure bG level on the display 408 and/or generating one or more other suitable types of reminders, such as audio, visual, and/or tactile alerts.

At 809, the processor module 504 determines whether a bG sample has already been provided for the waking time 604. If 809 is true, the processor module 504 suppresses generation of the reminder to measure bG level for that waking time 604 at 810, and control may end. If 809 is false, control may end. While control is shown and discussed as ending, FIG. 8 may be illustrative of one control loop, and control loops may be performed at a predetermined rate.

Figure 9:
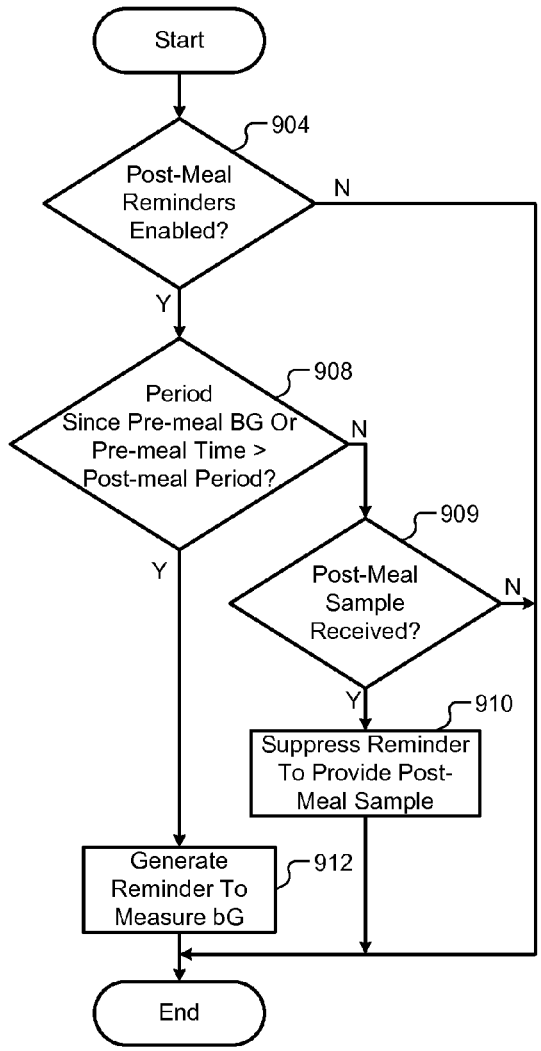
FIG. 9 includes a flowchart depicting an example method of generating a reminder to measure bG after a meal.

FIG. 9 is a flowchart depicting an example method of generating a reminder to measure bG after a meal (i.e., post-meal). At 904, the processor module 504 may determine whether reminders for post-meal bG measurements are enabled. The processor module 504 may determine whether reminders for post-meal bG measurements are enabled based on the post-meal enable/disable data 724. If 904 is true, control may continue with 908. If 904 is false, control may end.

At 908, the processor module 504 may determine whether the period between a time that a meal began and the present time is greater than the post-meal period 624. The present time may be stored as the time that the meal began when, for example, the user inputs an indicator of the beginning of the meal, such as via one or more of the user input devices 514, such as the buttons 424-436. Additionally or alternatively, the processor module 504 may determine whether the period between the time when a bG measurement provided for the meal (a pre-meal measurement) and the present time is greater than the post-meal period 624 at 908. If 908 is false, control may continue with 909. If 908 is true, the processor module 504 generates a reminder to measure bG level at 912, and control may end.

At 909, the processor module 504 determines whether a bG sample has already been provided after the meal. If 909 is true, the processor module 504 suppresses generation of the reminder to measure bG level after that meal at 910, and control may end. If 909 is false, control may end. While control is shown and discussed as ending, FIG. 9 may be illustrative of one control loop, and control loops may be performed at a predetermined rate.

Figure 10:
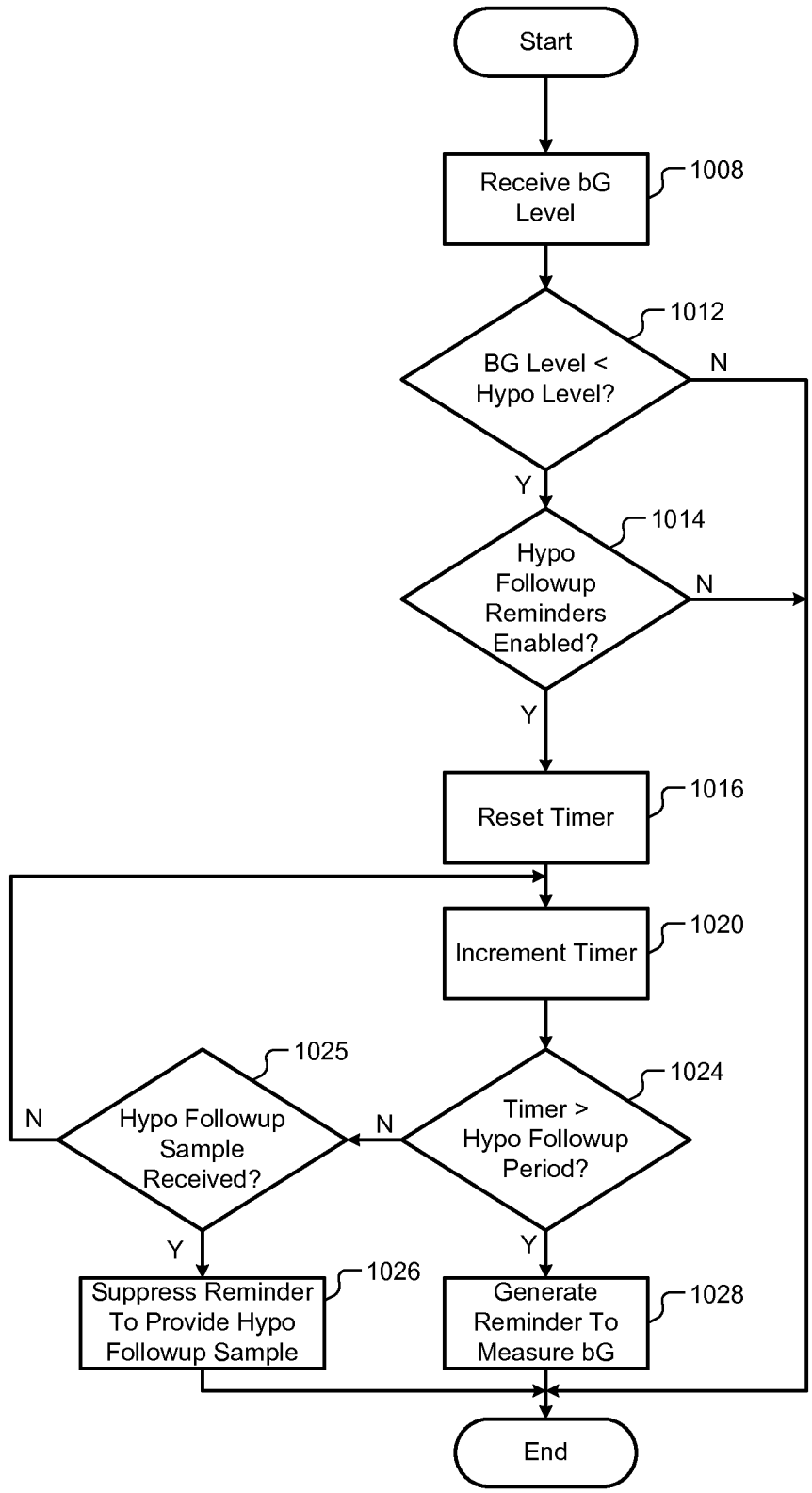
FIG. 10 includes an example method of generating a reminder to measure bG after a hypoglycemic bG measurement is provided.

FIG. 10 includes an example method of generating a reminder to measure bG after a hypoglycemic bG measurement is provided. At 1008, the processor module 504 receives the bG level of a blood sample present on a bG test strip. At 1012, the processor module 504 determines whether the bG level of the blood sample is less than the predetermined hypoglycemic bG level. If 1012 is true, control may continue with 1014. If 1012 is false, control may end.

At 1014, the processor module 504 may determine whether reminders for followup measurements after hypoglycemic bG measurements are enabled. The processor module 504 may determine whether reminders for followup measurements after hypoglycemic bG measurements are enabled based on the hypo followup enable/disable data 728. If 1014 is true, control may continue with 1016. If 1014 is false, control may end.

At 1016, the processor module 504 may reset a timer. The processor module 504 may increment the timer at 1020. The timer tracks the period since the hypoglycemic bG sample was received. At 1024, the processor module 504 determines whether the timer is greater than the hypo followup period 628. If 1024 is false, control may transfer to 1025. If 1024 is true, the processor module 504 generates a reminder to measure bG at 1028, and control may end.

At 1025, the processor module 504 determines whether a bG sample has already been provided following the hypoglycemic bG measurement. If 1025 is true, the processor module 504 suppresses generation of the reminder to measure bG level following the hypoglycemic measurement at 1026, and control may end. Of course, if that bG level is hypoglycemic too, the process may continue (e.g., return to 1016). If 1025 is false, control may transfer to 1020. While control is shown and discussed as ending, FIG. 10 may be illustrative of one control loop, and control loops may be performed at a predetermined rate.

Reminding the user to provide bG measurements regularly may help the user to provide bG measurements more consistently. bG measurements provided more regularly may be better analyzed for patterns/trends, and bG measurements provided more regularly may be used to more accurately provide suggestions as to actions to take at various points of a day to stabilize the user's bG level.

Referring back to FIG. 5, the processor module 504 may analyze the reminder data 548 determine whether the reminders are disabled. When the period between when the reminders were disabled is greater than a predetermined notification period, the processor module 504 may selectively display a notification on the display 408. The notification may indicate that the diabetes management device 402 can generate reminders for the events and prompt the user to provide input as to whether to enable or disable reminders for the events.

The processor module 504 selectively updates the data 704-728 based on the user input and updates the data 704-728 based on the present date and time if the user chooses to continue disabling the reminders. For example only, the predetermined notification period may be approximately 90 days or another suitable period.

Figure 11A:
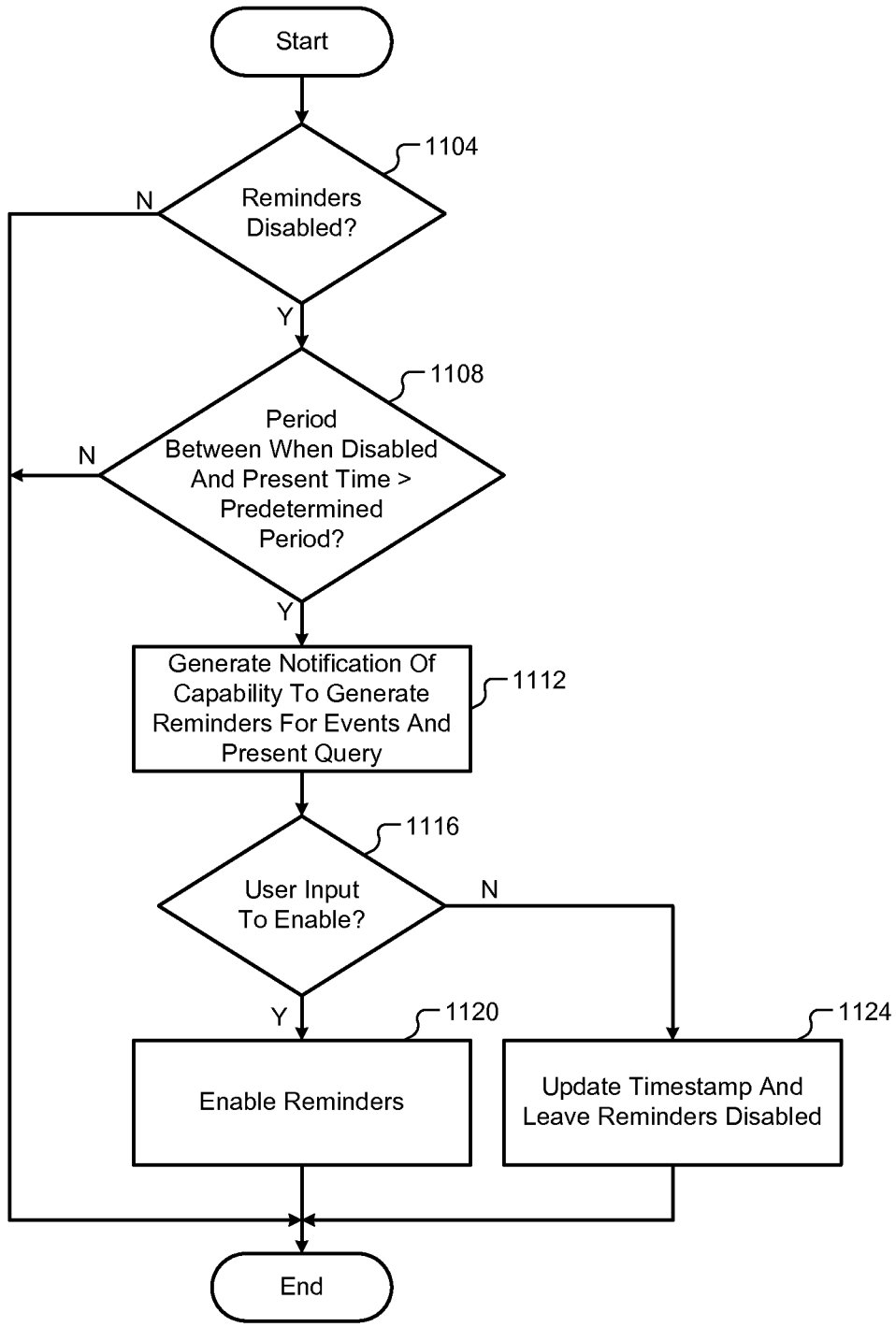
FIG. 11A includes a flowchart depicting an example method of notifying a user that a diabetes management device is capable of providing reminders for events.

FIG. 11A is a flowchart depicting an example method of notifying a user that the diabetes management device 402 is capable of providing reminders for the events. At 1104, the processor module 504 may determine whether the reminders are disabled. The processor module 504 may determine whether the reminders are disabled based on the reminder data 548. If 1104 is true, control may continue with 1108. If 1104 is false, control may end.

At 1108, the processor module 504 may determine whether the period between the date and time when the reminders were disabled and the present date and time is greater than the predetermined notification period. If 1108 is false, control may end. If 1108 is true, control may continue with 1112.

At 1112, the processor module 504 generates the notification that the diabetes management device 402 is capable of reminding the user to measure their bG level for each of the events. The notification may include, for example, a visual notification on the display 408. The processor module 504 may also query the user at 1112 as to whether the user desires the reminders for the events to be enabled.

At 1116, the processor module 504 may determine whether the user's response to the query indicates that the user desires to enable the reminders. If 1116 is true (indicating that the user desired to enable the reminders), the processor module 504 may update the reminder data 548 to enable the reminders for the events at 1120, and control may end. If 1116 is false (indicating that the user desired to maintain the reminders disabled), the processor module 504 stores the present date and time at 1124, and control may end. The notification may be generated again in the future (the predetermined notification period after the stored date and time) if the reminders are not first enabled. While control is shown and discussed as ending, FIG. 11A may be illustrative of one control loop, and control loops may be performed at a predetermined rate.

Figure 11B:
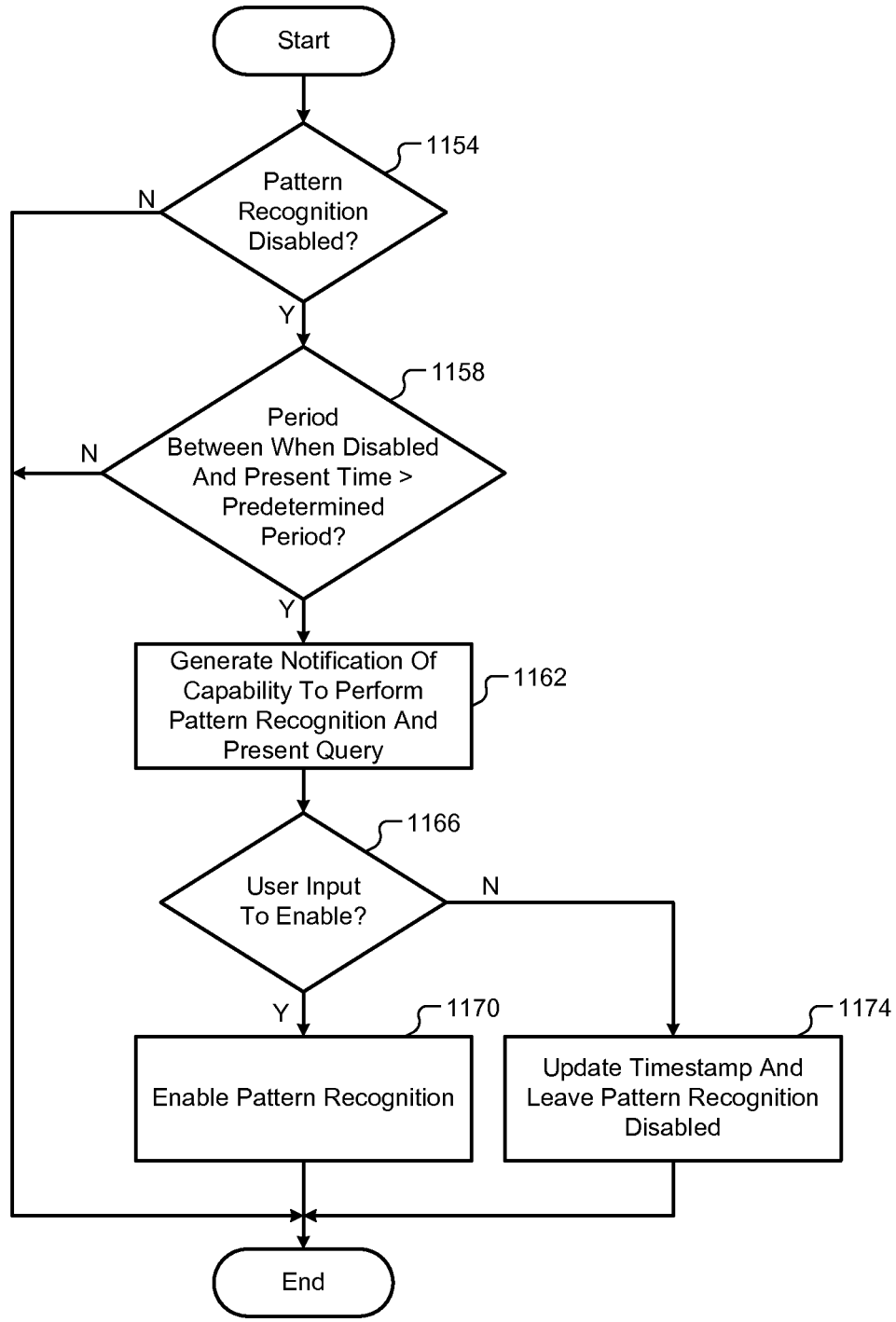
FIG. 11B includes a flowchart depicting an example method of notifying a user that a diabetes management device is capable of performing pattern recognition.

FIG. 11B is a flowchart depicting an example method of notifying a user that the diabetes management device 402 is capable of performing pattern recognition in bG samples. At 1154, the processor module 504 may determine whether pattern recognition is disabled. The user can enable and disable pattern recognition via one or more of the user input devices 514. Pattern recognition is described in further detail below. The processor module 504 may determine whether pattern recognition is disabled based on pattern data 560. If 1154 is true, control may continue with 1158. If 1154 is false, control may end.

At 1158, the processor module 504 may determine whether the period between the date and time when pattern recognition was disabled and the present date and time is greater than the predetermined notification period. If 1158 is false, control may end. If 1158 is true, control may continue with 1162.

At 1162, the processor module 504 generates the notification that the diabetes management device 402 is capable of performing pattern recognition. The notification may include, for example, a visual notification on the display 408. The processor module 504 may also query the user at 1162 as to whether the user desires pattern recognition to be enabled.

At 1166, the processor module 504 may determine whether the user's response to the query indicates that the user desires to enable pattern recognition. If 1166 is true (indicating that the user desired to enable pattern recognition), the processor module 504 may update the pattern data 560 to enable pattern recognition at 1170, and control may end. If 1166 is false (indicating that the user desired to maintain pattern recognition disabled), the processor module 504 stores the present date and time at 1174, and control may end. The notification may be generated again in the future (the predetermined notification period after the stored date and time) if pattern recognition is not first enabled. While control is shown and discussed as ending, FIG. 11B may be illustrative of one control loop, and control loops may be performed at a predetermined rate.

Referring back to FIG. 5, the processor module 504 also selectively classifies the bG sample data 516 as one of a waking measurement, a pre-breakfast measurement, a post-breakfast measurement, a pre-lunch measurement, a post-lunch measurement, a pre-dinner measurement, a post-dinner measurement, or a bed time measurement. Waking measurements may also be referred to as fasting measurements. However, fasting measurements may also include measurements taken when a period of fasting occurred prior to measurement. The processor module 504 classifies the bG sample data 516 based on the timestamp included in the bG sample data 516 and the timing data 544 associated with the events. The processor module 504 may update the bG sample data 516 to include an indicator of the classification or may store an indicator of the classification and relate the indicator with the bG sample data 516.

The processor module 504 performs this process for each bG sample measured by the bG measurement engine 508. The processor module 504 can select bG sample data associated with one or more of the events based on the classifications, as discussed below. The processor module 504 determines the classification for each bG sample using classification rule data 552. The classification rule data 552 includes data indicating what data to use and rules for how to classify bG sample data.

For example, the processor module 504 may classify the bG sample data 516 as a waking measurement when the timestamp of the bG sample data 516 is within a predetermined period before or within a predetermined time period around the waking time 604. The processor module 504 may classify the bG sample data 516 as a bed time measurement when the timestamp of the bG sample data 516 is within a predetermined period after or within a predetermined time period around the bed time 620.

The processor module 504 may classify the bG sample data 516 as a pre-meal measurement of a meal when the timestamp of the bG sample data 516 is within a predetermined time window around the one of the times 608-616 associated with the meal. For example, the processor module 504 may classify the bG sample data 516 as a pre-breakfast measurement when the timestamp of the bG sample data 516 is within a predetermined time window around the breakfast time 608. The processor module 504 may classify the bG sample data 516 as a pre-lunch measurement when the timestamp of the bG sample data 516 is within a predetermined time window around the lunch time 612. The processor module 504 may classify the bG sample data 516 as a pre-dinner measurement when the timestamp of the bG sample data 516 is within a predetermined time window around the dinner time 616.

The processor module 504 may classify the bG sample data 516 as a post-meal measurement of a meal when the timestamp of the bG sample data 516 is within the post-meal period 624 after the timestamp of another piece of bG sample data that is classified as a pre-meal sample of that meal. For example, the processor module 504 may classify the bG sample data 516 as a post-breakfast measurement when the timestamp of the bG sample data 516 is within the post-meal period 624 after the timestamp of a second piece of bG sample data that is classified as a pre-breakfast measurement. The processor module 504 may classify the bG sample data 516 as a post-lunch measurement when the timestamp of the bG sample data 516 is within the post-meal period 624 after the timestamp of a second piece of bG sample data that is classified as a pre-lunch measurement. The processor module 504 may classify the bG sample data 516 as a post-dinner measurement when the timestamp of the bG sample data 516 is within the post-meal period 624 after the timestamp of a second piece of bG sample data that is classified as a pre-dinner measurement.

The processor module 504 may prompt the user to select one of the classifications for bG sample data that could be classified in multiple different ways and set the classification for the bG sample data based on the user input. The processor module 504 may also selectively update the classification determined for bG sample data based on use input indicative of one of the classifications. In this manner, the user can overwrite the classification determined for bG sample data.

The automated classification of bG sample data performed by the processor module 504 may ensure that bG sample data is classified in the event that the user does not provide the classification. The automated classification of bG sample data performed by the processor module 504 may also provide for less frequent user classifications.

The processor module 504 may determine the classification for the bG sample data 516 and store the indicator of the classification before displaying the bG level of the bG sample data 516. The processor module 504 may determine the classification and store the indicator, for example, before a blood sample is applied to a test strip or after the bG level is determined but before the bG level is displayed. Classifying the bG sample data 516 and storing the indicator before displaying the bG level may make testing more hygienic as the user may not need to self-classify bG sample data at a time when the user may or may not have blood on a finger used to provide the blood sample.

The processor module 504 selectively performs statistical analysis functions based on the stored bG sample data 540. The processor module 504 may perform a statistical analysis and display one or more results of the statistical analysis on the display 408, for example, when the user requests performance of the statistical analysis.

The processor module 504 performs statistical analyses using statistics data 556. The statistics data 556 includes data indicating which bG levels stored in the memory 532 to use and rules for performing the statistical analyses. A statistical analysis may be performed without regard to the classification of the stored bG levels used or using stored bG levels selected for having one or more of the classifications.

The processor module 504 may, for example, determine an average of the stored bG levels. Additionally or alternatively, the processor module 504 may determine a standard deviation of the stored bG levels. Additionally or alternatively, the processor module 504 may determine a ratio or percentage of the stored bG levels that are less than the predetermined hypoglycemic level, a ratio or percentage of the stored bG levels that are greater than the predetermined hyperglycemic level, and/or a ratio or percentage of the bG levels stored that are between a target higher bG level and a target lower bG level. Additionally or alternatively, the processor module 504 may determine a frequency of hypoglycemic bG samples and/or a frequency of hyperglycemic bG samples based on the stored bG levels.

The processor module 504 may also selectively display more detailed information for the stored bG levels used to perform a statistical analysis on the display 408. For example, the processor module 504 may selectively display the time and date, the bG level, and the classification of bG sample data used in performing a statistical analysis. The processor module 504 may display the more detailed information, for example, in response to user input requesting that the more detailed information be displayed.

The processor module 504 also selectively performs pattern recognition functions based on the stored bG sample data 540. The processor module 504 may perform pattern recognition, for example, each time a bG measurement is provided.

The processor module 504 performs pattern recognition using pattern data 560. The pattern data 560 includes data indicating which bG sample data stored in the memory 532 to use (select) and rules for identifying patterns in the stored bG sample data. Pattern recognition may be performed, for example, using stored bG sample data having the same classification as the most recently received bG measurement.

The processor module 504 selects stored bG sample data that is classified the same way as the most recently received bG measurement. The processor module 504 may select, for example, stored bG sample data that has the same classification as the most recently received bG measurement and that was received within the most recent predetermined period (e.g., 3-7 days). As an example of the selection, when a pre-lunch sample is received, the processor module 504 may select bG sample data for blood samples classified as pre-lunch samples that were received within the last 7 days.

The processor module 504 determines whether a pattern is present based on whether the selected bG sample data satisfies predetermined pattern criteria. For example, the processor module 504 may determine that a high pre-meal bG pattern is present when more than a first predetermined number (e.g., at least 3 or 4 when a period of 7 days is used) of pieces of the selected bG sample data (the bG sample data selected as having that pre-meal classification) have bG levels that are greater than a first predetermined bG value. The meal can be breakfast, lunch, dinner, or optionally a fourth-meal, such as tea. The processor module 504 may determine that a low pre-meal bG pattern is present when more than a second predetermined number (e.g., at least 2 when a period of 7 days is used) of pieces of the selected bG sample data (the bG sample data selected as having that pre-meal classification) have bG levels that are less than a second predetermined bG value. As with high pre-meal bG patterns, for low pre-meal bG patterns, the meal can be breakfast, lunch, dinner, or optionally a fourth-meal. The first predetermined bG value is greater than the second predetermined bG value. The processor module 504 may determine that a high post-meal bG pattern is present when more than the first predetermined number (e.g., at least 3 or 4 when a period of 7 days is used) of pieces of the selected bG sample data (the bG sample data selected as having that pre-meal classification) have bG levels that are greater than a third predetermined bG value. The meal can be breakfast, lunch, dinner, or optionally a fourth-meal, such as tea. The processor module 504 may determine that a low post-meal bG pattern is present when more than the second predetermined number (e.g., at least 2 when a period of 7 days is used) of pieces of the selected bG sample data (the bG sample data selected as having that pre-meal classification) have bG levels that are less than a fourth predetermined bG value. As with high post-meal bG patterns, for low post-meal bG patterns, the meal can be breakfast, lunch, dinner, or optionally a fourth-meal. The third predetermined bG value is greater than the fourth predetermined bG value. When a pattern is recognized, the processor module 504 stores an indicator of the recognized pattern and the selected bG sample data based upon which the pattern was recognized in the memory 532, such as in the pattern data 560.

The processor module 504 selectively displays recognized patterns on the display 408. When a pattern is recognized based on the selected bG sample data, the processor module 504 displays an indication of the pattern on the display 408. For example, the processor module 504 may display an indication that a high or low pre- or post-meal pattern is present when the high or low pre- or post-meal pattern is recognized.

The processor module 504 may also query the user to input an acknowledgement of the recognized pattern and to view details of the bG sample data based upon which the pattern was recognized. In response to user input indicative of an acknowledgement of the recognized pattern, the processor module 504 displays details of the selected bG sample data based on which the pattern was recognized. The details may include, for example, date and time of measurement of a sample, bG level, the associated target bG level, and other suitable details. The processor module 504 may display the details, for example, one piece of bG sample data at a time.

FIG. 12 includes a flowchart depicting an example method of identifying and displaying a pattern in bG sample data. At 1202, the diabetes management device 402 receives a bG sample. The processor module 504 may determine a classification for the bG sample or the classification of the bG sample may be set based on user input indicative of the classification.

At 1204, the processor module 504 selects a set of stored bG sample data. The processor module 504 may, for example, select the set of stored bG sample data based on classification, time stamps, and/or other suitable parameters. For example, the processor module 504 may select stored bG sample data having the same classification as the bG sample received (at 1202) and received within the last predetermined period (e.g., 7 days). For clarity, it should be noted that the bG sample data associated with the bG sample received at 1202 is one of the pieces of bG sample data that is selected.

At 1208, the processor module 504 determines whether a pattern is present based on the selected set of stored bG sample data. If 1208 is true, the processor module 504 stores an indicator of the recognized pattern in the memory 532 and continues with 1216. If 1208 is false, control may end. At 1216, the processor module 504 displays identified pattern on the display 408. The processor module 504 also queries the user at 1216 to provide input indicating an acknowledgement of the identified pattern.

At 1220, the processor module 504 determines whether user input indicative of an acknowledgement of the presence of the identified pattern has been received. If 1220 is false, control returns to 1216, and the processor module 504 continues to display the identified pattern. If 1220 is true, the processor module 504 may continue with 1222. At 1222, the processor module 504 selectively displays details of the selected set of stored bG sample data, such as date and time, bG level, etc. The processor module 504 then allows the user to clear the identified pattern from the display 408 at 1224, and control may end.

Referring back to FIG. 5, when the processor module 504 recognizes the presence of a pattern based on stored bG sample data having one classification, the processor module 504 may identify a daily event preceding the event associated with the classification. For example, when the processor module 504 recognizes the presence of a high or low bG pattern based on pre-lunch bG samples, the processor module may identify breakfast as a previous event.

The next time that a bG sample is provided for the previous event, the processor module 504 displays an indicator of that recognized pattern at the event associated with the classification. For example, at the breakfast following the lunch when a pattern was recognized, the processor module 504 may display an indicator that a high or low bG pattern was recognized at the previous lunch. In the above example, the high or low bG pattern may be attributable to meal consumption at breakfast. Providing the indication of the recognized pattern at breakfast may help the user adjust his or her breakfast to prevent having a high or low pre-lunch bG level at the following lunch.

FIG. 13 includes a flowchart depicting an example method of, based on recognition of a pattern associated with a daily event, displaying a reminder of the presence of the pattern at an event before that event. At 1304 the processor module 504 determines whether a pattern is present based on a selected set of stored bG sample data, as discussed above in conjunction with FIG. 12. As discussed above, the selected set of bG sample data has one classification and is associated with a daily event, such as lunch. If 1304 is true, control continues with 1308. If 1304 is false, control may end.

At 1308, the processor module 504 determines the daily event that precedes the daily event associated with the selected set of bG sample data based on which the pattern was recognized. For example, if the selected set of bG sample data is associated with lunch, the processor module 504 may determine that the preceding daily event is breakfast. At 1312, the processor module 504 sets a flag or other indicator to display the presence of the recognized pattern at the next instance of the preceding daily event. For example, if the selected set of bG sample data is associated with lunch, the processor module 504 may set the flag or other indicator to display the presence of the recognized pattern at the next breakfast following the lunch where the pattern was recognized.

At 1316, the processor module 504 may determine whether the next occurrence of the preceding daily event (e.g., the next breakfast) is present. For example, the processor module 504 may determine that the next occurrence of the preceding daily event is present at the predetermined time associated with the preceding event and/or based on user input indicative of the next occurrence of the preceding daily event. If 1316 is false, control may remain at 1316. If 1316 is true, control may continue with 1318. At 1318, the order of display of recognized patterns may be prioritized. For example, the processor module 504 may prioritize low bG patterns over high bG patterns, prioritize recognized patterns according to the daily order of the event (e.g., breakfast patterns before lunch patterns, etc.), and/or prioritize newer patterns over older patterns.

The processor module 504 displays an indicator of the recognized pattern(s) associated with the next event at 1320, and control may end. For example, at the next breakfast following recognition of a high or low pre-lunch bG pattern, the processor module 504 may display the presence of the high or low pre-lunch bG pattern. The user can then adjust their breakfast intake in an effort to decrease or increase their pre-lunch bG level of the following lunch.

Referring back to FIG. 5, the processor module 504 may also display previously recognized patterns in response to user input indicative of a desire to view previously recognized patterns. For example, the processor module 504 may generate a list of currently active patterns recognized within a most recent predetermined period and display the list of recognized patterns. The predetermined period may be, for example, 7 days or another suitable period.

Based on user input selecting one of the patterns from the list, the processor module 504 may display details of the stored bG sample data underlying the selected one of the patterns. The processor module 504 also prioritizes the order in which recognized patterns are displayed. For example, the processor module 504 displays low bG patterns before high bG patterns, patterns for earlier daily events before patterns for later daily events (e.g., breakfast patterns before lunch patterns), and/or newer patterns before older patterns.

Figure 14:
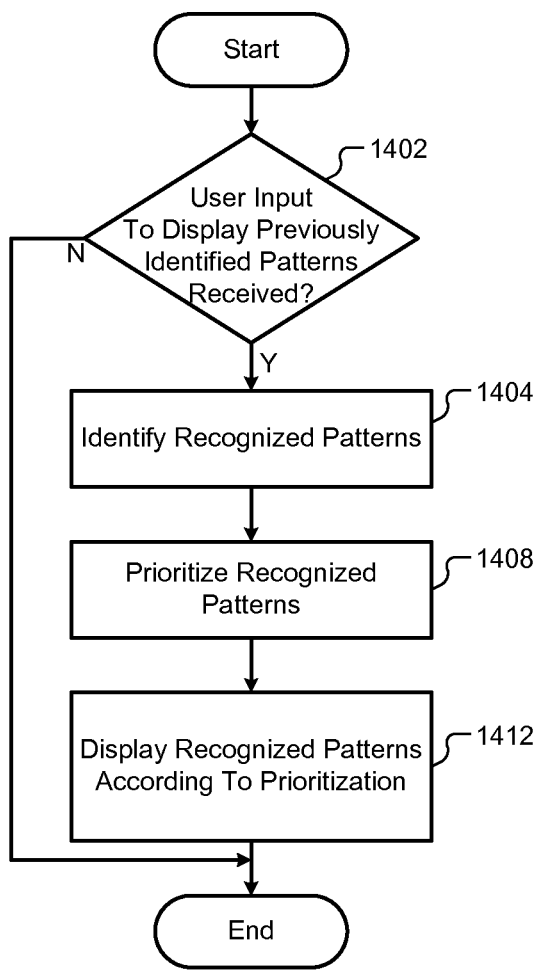
FIG. 14 includes a flowchart depicting an example method of displaying previously recognized patterns in bG sample data.

FIG. 14 includes a flowchart depicting an example method of displaying previously recognized patterns in bG sample data. At 1402, the processor module 504 may determine whether user input has been received requesting that previously identified patterns be displayed. If 1402 is true, control continues with 1404. If 1402 is false, control may end.

At 1404, the processor module 504 identifies previously recognized patterns. For example, the processor module 504 may identify patterns recognized within the last predetermined period, such as 3 months, 6 months, 9 months, 1 year, or another suitable period. At 1408, the processor module 504 prioritizes the previously recognized patterns for display.

At 1412, the processor module 504 displays the list of recognized patterns on the display 408 according to the prioritization. Based on user input selecting one of the patterns from the list, the processor module 504 may display details of the stored bG sample data underlying the selected one of the patterns. The processor module 504 may display, for example, the time and date of underlying bG samples, the bG levels of underlying bG samples, and other suitable data.

In a feature, a method for classifying blood samples and identifying medically relevant patterns in groups of blood samples is disclosed. The method includes: measuring a blood glucose (bG) level in a blood sample received by a handheld diabetes management device; storing the bG level and a time of receipt of the blood sample in memory; storing a classification of the blood sample, wherein the classification is one of a fasting sample, a pre-breakfast sample, a post-breakfast sample, a pre-lunch sample, a post-lunch sample, a pre-dinner sample, a post-dinner sample, and a bed time sample; and in response to the receipt of the blood sample, selecting a group of stored bG levels having the classification of the blood sample and that were received within a predetermined period before receipt of the blood sample. The method further includes: calculating a bG evaluation parameter from the selected bG levels; evaluating the bG evaluation parameter in relation to first predetermined criteria, the first predetermined criteria including a first threshold indicative of a high bG level or a low bG level; selectively displaying an indication of recognition of a pattern in the selected bG levels when the bG evaluation parameter is greater than or less than the first threshold; and removing the indication from the display only in response to receipt of predetermined user input indicative of an acknowledgement of the presence of the pattern.

In further features, the method further includes storing the classification based on user input indicative of the classification.

In still further features, the method further includes, when reminder data associated with one of the classifications is enabled, displaying a reminder to provide a blood sample at a predetermined time associated with the one of the classifications.

In yet further features, the method further includes updating the reminder data based on user input indicative of whether to display reminders to provide a blood sample at the predetermined time.

In further features, the method further includes determining the classification for the blood sample based on the time of receipt of the blood sample.

In still further features, the method further includes determining that the classification of the blood sample is a fasting sample when the time of receipt of the blood sample is within a predetermined time window around a predetermined time associated with fasting samples.

In yet further features, the method further includes determining that the classification of the blood sample is a pre-breakfast sample when the time of receipt of the blood sample is within a predetermined time window around a predetermined time associated with breakfast.

In further features, the method further includes comprising determining that the classification of the blood sample is a post-breakfast sample when the time of receipt of the blood sample is within a predetermined period after a second time of receipt of a second blood sample classified as a pre-breakfast sample.

In still further features, the method further includes determining that the classification of the blood sample is a post-breakfast sample when the time of receipt of the blood sample is within a predetermined period after a second time of receipt of user input indicative of a start of breakfast.

In yet further features, the method further includes determining that the classification of the blood sample is a pre-lunch sample when the time of receipt of the blood sample is within a predetermined time window around a predetermined time associated with lunch.

In further features, the method further includes determining that the classification of the blood sample is a post-lunch sample when the time of receipt of the blood sample is within a predetermined period after a second time of receipt of a second blood sample classified as a pre-lunch sample.

In still further features, the method further includes determining that the classification of the blood sample is a post-lunch sample when the time of receipt of the blood sample is within a predetermined period after a second time of receipt of user input indicative of a start of lunch.

In yet further features, the method further includes determining that the classification of the blood sample is a pre-dinner sample when the time of receipt of the blood sample is within a predetermined time window around a predetermined time associated with dinner.

In further features, the method further includes determining that the classification of the blood sample is a post-dinner sample when the time of receipt of the blood sample is within a predetermined period after a second time of receipt of a second blood sample classified as a pre-dinner sample.

In still further features, the method further includes determining that the classification of the blood sample is a post-dinner sample when the time of receipt of the blood sample is within a predetermined period after a second time of receipt of user input indicative of a start of dinner.

In yet further features, the method further includes determining that the classification of the blood sample is a bed time sample when a time stamp of the blood sample is within a predetermined time window around a predetermined time associated with bed time samples.

In further features, the method further includes: displaying the bG level of the blood sample; and, before displaying the bG level, determining the classification of the blood sample.

In still further features, the method further includes: determining a first daily event preceding a second daily event associated with the classification; and, during a day following the receipt of the blood sample, displaying the indication of the pattern in the selected bG levels at a time associated with the first daily event.

In a feature, a handheld diabetes management device for classifying blood samples and identifying medically relevant patterns in groups of blood samples is disclosed. The handheld diabetes management includes: a blood glucose (bG) measurement engine that measures bG levels in blood samples input to the handheld diabetes management device; a display; a clock tracking a present date and time; a processor; and memory including code executed by the processor. The code is for: storing the bG level and a time of receipt of the blood sample in memory; storing a classification of the blood sample, wherein the classification is one of a fasting sample, a pre-breakfast sample, a post-breakfast sample, a pre-lunch sample, a post-lunch sample, a pre-dinner sample, a post-dinner sample, and a bed time sample; in response to the receipt of the blood sample, selecting a group of stored bG levels having the classification of the blood sample and that were received within a predetermined period before receipt of the blood sample; calculating a bG evaluation parameter from the selected bG levels; evaluating the bG evaluation parameter in relation to first predetermined criteria, the first predetermined criteria including a first threshold indicative of a high bG level or a low bG level; and selectively displaying an indication of recognition of a pattern in the selected bG levels when the bG evaluation parameter is greater than or less than the first threshold.

In further features, the memory further includes code for determining the classification for the blood sample based on the time of receipt of the blood sample.

In still further features, the memory further includes code for storing the classification for the blood sample based on user input indicative of the classification.

In yet further features, the memory further includes code for: displaying the bG level of the blood sample; and, before displaying the bG level, determining the classification of the blood sample.

In further features, the memory further includes code for, when reminder data associated with one of the classifications is enabled, displaying a reminder to provide a blood sample at a predetermined time associated with the one of the classifications.

In still further features, the memory further includes code for updating the reminder data based on user input indicative of whether to display reminders to provide a blood sample at the predetermined time.

In yet further features, the memory further includes code for: determining a first daily event preceding a second daily event associated with the classification; and, during a day following the receipt of the blood sample, displaying the indication of the pattern in the selected bG levels at a time associated with the first daily event.

In a feature, a method for classifying blood samples and identifying medically relevant patterns in groups of blood samples is disclosed. The method includes: measuring a blood glucose (bG) level in a blood sample received by a handheld diabetes management device; storing the bG level and a time of receipt of the blood sample in memory; storing a classification of the blood sample, wherein the classification is one of a fasting sample, a pre-breakfast sample, a post-breakfast sample, a pre-lunch sample, a post-lunch sample, a pre-dinner sample, a post-dinner sample, and a bed time sample; selecting a group of stored bG levels having one of the classifications; and generating an indicator of recognition of a pattern in the selected group of bG levels when a bG evaluation parameter calculated based on the selected bG levels is one of greater than a first threshold indicative of a high bG level and less than a second threshold indicative of a low bG level. The method further includes, in response to a user request to display recognized patterns in bG levels: generating a list of recognized patterns including the pattern in the selected bG levels; prioritizing the list based on predetermined prioritization criteria; and displaying the list on the display.

In further features, the method further includes storing the classification based on user input indicative of the classification.

In still further features, the method further includes, when reminder data associated with one of the classifications is enabled, displaying a reminder to provide a blood sample at a predetermined time associated with the one of the classifications.

In yet further features, the method further includes updating the reminder data based on user input indicative of whether to display reminders to provide a blood sample at the predetermined time.

In further features, the method further includes determining the classification for the blood sample based on the time of receipt of the blood sample.

In still further features, the method further includes determining that the classification of the blood sample is a fasting sample when the time of receipt of the blood sample is within a predetermined time window around a predetermined time associated with fasting samples.

In yet further features, the method further includes determining that the classification of the blood sample is a pre-breakfast sample when the time of receipt of the blood sample is within a predetermined time window around a predetermined time associated with breakfast.

In further features, the method further includes determining that the classification of the blood sample is a post-breakfast sample when the time of receipt of the blood sample is within a predetermined period after a second time of receipt of a second blood sample classified as a pre-breakfast sample.

In still further features, the method further includes determining that the classification of the blood sample is a post-breakfast sample when the time of receipt of the blood sample is within a predetermined period after a second time of receipt of user input indicative of a start of breakfast.

In yet further features, the method further includes determining that the classification of the blood sample is a pre-lunch sample when the time of receipt of the blood sample is within a predetermined time window around a predetermined time associated with lunch.

In further features, the method further includes determining that the classification of the blood sample is a post-lunch sample when the time of receipt of the blood sample is within a predetermined period after a second time of receipt of a second blood sample classified as a pre-lunch sample.

In still further features, the method further includes determining that the classification of the blood sample is a post-lunch sample when the time of receipt of the blood sample is within a predetermined period after a second time of receipt of user input indicative of a start of lunch.

In yet further features, the method further includes determining that the classification of the blood sample is a pre-dinner sample when the time of receipt of the blood sample is within a predetermined time window around a predetermined time associated with dinner.

In further features, the method further includes determining that the classification of the blood sample is a post-dinner sample when the time of receipt of the blood sample is within a predetermined period after a second time of receipt of a second blood sample classified as a pre-dinner sample.

In still further features, the method further includes determining that the classification of the blood sample is a post-dinner sample when the time of receipt of the blood sample is within a predetermined period after a second time of receipt of user input indicative of a start of dinner.

In yet further features, the method further includes determining that the classification of the blood sample is a bed time sample when a time stamp of the blood sample is within a predetermined time window around a predetermined time associated with bed time samples.

In further features, the method further includes: displaying the bG level of the blood sample; and, before displaying the bG level, determining the classification of the blood sample.

In still further features, the method further includes: determining a first daily event preceding a second daily event associated with the classification; and, during a day following the receipt of the blood sample, displaying the indication of the pattern in the selected bG levels at a time associated with the first daily event.

In a feature, a handheld diabetes management device for classifying blood samples and identifying medically relevant patterns in groups of blood samples is disclosed. The handheld diabetes management device includes: a blood glucose (bG) measurement engine that measures bG levels in blood samples input to the handheld diabetes management device; a display; a clock tracking a present date and time; a processor; and memory including code executed by the processor. The code is for: measuring a blood glucose (bG) level in a blood sample received by the handheld diabetes management device; storing the bG level and a time of receipt of the blood sample in memory; storing a classification of the blood sample, wherein the classification is one of a fasting sample, a pre-breakfast sample, a post-breakfast sample, a pre-lunch sample, a post-lunch sample, a pre-dinner sample, a post-dinner sample, and a bed time sample;

selecting a group of stored bG levels having one of the classifications; and generating an indicator of recognition of a pattern in the selected group of bG levels when a bG evaluation parameter calculated based on the selected bG levels is one of greater than a first threshold indicative of a high bG level and less than a second threshold indicative of a low bG level. The code is further for, in response to a user request to display recognized patterns in bG levels: generating a list of recognized patterns including the pattern in the selected bG levels; prioritizing the list based on predetermined prioritization criteria; and displaying the list on the display.

In further features, the memory further includes code for determining the classification for the blood sample based on the time of receipt of the blood sample.

In still further features, the memory further includes code for storing the classification for the blood sample based on user input indicative of the classification.

In yet further features, the memory further includes code for: displaying the bG level of the blood sample; and, before displaying the bG level, determining the classification of the blood sample.

In further features, the memory further includes code for, when reminder data associated with one of the classifications is enabled, displaying a reminder to provide a blood sample at a predetermined time associated with the one of the classifications.

In still further features, the memory further includes code for updating the reminder data based on user input indicative of whether to display reminders to provide a blood sample at the predetermined time.

In yet further features, the memory further includes code for: determining a first daily event preceding a second daily event associated with the classification; and, during a day following the receipt of the blood sample, displaying the indication of the pattern in the selected bG levels at a time associated with the first daily event.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. As used herein, the phrase at least one of A, B, and C should be construed to mean a logical (A or B or C), using a non-exclusive logical OR. It should be understood that one or more steps within a method may be executed in different order (or concurrently) without altering the principles of the present disclosure.

In this application, including the definitions below, the term module may be replaced with the term circuit. The term module may refer to, be part of, or include an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor (shared, dedicated, or group) that executes code; memory (shared, dedicated, or group) that stores code executed by a processor; other suitable hardware components that provide the described functionality; or a combination of some or all of the above, such as in a system-on-chip.

The term code, as used above, may include software, firmware, and/or microcode, and may refer to programs, routines, functions, classes, and/or objects. The term shared processor encompasses a single processor that executes some or all code from multiple modules. The term group processor encompasses a processor that, in combination with additional processors, executes some or all code from one or more modules. The term shared memory encompasses a single memory that stores some or all code from multiple modules. The term group memory encompasses a memory that, in combination with additional memories, stores some or all code from one or more modules. The term memory may be a subset of the term computer-readable medium. The term computer-readable medium does not encompass transitory electrical and electromagnetic signals propagating through a medium, and may therefore be considered tangible and non-transitory. Non-limiting examples of a non-transitory tangible computer readable medium include nonvolatile memory, volatile memory, magnetic storage, and optical storage.

The apparatuses and methods described in this application may be partially or fully implemented by one or more computer programs executed by one or more processors. The computer programs include processor-executable instructions that are stored on at least one non-transitory tangible computer readable medium. The computer programs may also include and/or rely on stored data.

What is claimed is:

1. A method for classifying blood samples and identifying medically relevant patterns in groups of blood samples, the method comprising:

measuring, by a blood glucose (bG) measurement engine of a handheld diabetes management device, a bG level in a blood sample received by the handheld diabetes management device via a bG test strip;

by a processor of the handheld diabetes management device, storing the bG level and a time of receipt of the blood sample in memory of the handheld diabetes management device;

by the processor, determining a classification of the blood sample based on a time the blood sample;

by the processor, storing the classification of the blood sample in the memory, wherein the classification is one of a fasting sample, a pre-breakfast sample, a post-breakfast sample, a pre-lunch sample, a post-lunch sample, a pre-dinner sample, a post-dinner sample, and a bed time sample;

by the processor, in response to the receipt of the blood sample, selecting a group of stored bG levels having the classification of the blood sample and that were received within a predetermined period before receipt of the blood sample;

by the processor, calculating a bG evaluation parameter from the selected bG levels;

by the processor, evaluating the bG evaluation parameter in relation to first predetermined criteria, the first predetermined criteria including a first threshold indicative of a high bG level or a low bG level;

by the processor, selectively displaying, on a display of the handheld diabetes management device, an indication of recognition of a pattern in the selected bG levels when the bG evaluation parameter is greater than or less than the first threshold; and by the processor, removing the indication from the display only in response to receipt of predetermined user input indicative of an acknowledgement of the presence of the pattern.

2. The method of claim 1 further comprising, when reminder data associated with one of the classifications is enabled, displaying a reminder to provide a blood sample at a predetermined time associated with the one of the classifications.

3. The method of claim 2, further comprising updating the reminder data based on user input indicative of whether to display reminders to provide a blood sample at the predetermined time.

4. The method of claim 1 further comprising determining that the classification of the blood sample is a fasting sample when the time of receipt of the blood sample is within a predetermined time window around a predetermined time associated with fasting samples.

5. The method of claim 1 further comprising determining that the classification of the blood sample is a pre-breakfast sample when the time of receipt of the blood sample is within a predetermined time window around a predetermined time associated with breakfast.

6. The method of claim 5 further comprising determining that the classification of the blood sample is a post-breakfast sample when the time of receipt of the blood sample is within a predetermined period after a second time of receipt of a second blood sample classified as a pre-breakfast sample.

7. The method of claim 1 further comprising determining that the classification of the blood sample is a post-breakfast sample when the time of receipt of the blood sample is within a predetermined period after a second time of receipt of user input indicative of a start of breakfast.

8. The method of claim 1 further comprising determining that the classification of the blood sample is a pre-lunch sample when the time of receipt of the blood sample is within a predetermined time window around a predetermined time associated with lunch.

9. The method of claim 8 further comprising determining that the classification of the blood sample is a post-lunch sample when the time of receipt of the blood sample is within a predetermined period after a second time of receipt of a second blood sample classified as a pre-lunch sample.

10. The method of claim 1 further comprising determining that the classification of the blood sample is a post-lunch sample when the time of receipt of the blood sample is within a predetermined period after a second time of receipt of user input indicative of a start of lunch.

11. The method of claim 1 further comprising determining that the classification of the blood sample is a pre-dinner sample when the time of receipt of the blood sample is within a predetermined time window around a predetermined time associated with dinner.

12. The method of claim 11 further comprising determining that the classification of the blood sample is a post-dinner sample when the time of receipt of the blood sample is within a predetermined period after a second time of receipt of a second blood sample classified as a pre-dinner sample.

13. The method of claim 1 further comprising determining that the classification of the blood sample is a post-dinner sample when the time of receipt of the blood sample is within a predetermined period after a second time of receipt of user input indicative of a start of dinner.

14. The method of claim 1 further comprising determining that the classification of the blood sample is a bed time sample when a time stamp of the blood sample is within a predetermined time window around a predetermined time associated with bed time samples.

15. The method of claim 1 further comprising:
displaying the bG level of the blood sample; and,
before displaying the bG level, determining the classification of the blood sample.

16. The method of claim 1 further comprising:
determining a first daily event preceding a second daily event associated with the classification; and,
during a day following the receipt of the blood sample, displaying the indication of the pattern in the selected bG levels at a time associated with the first daily event.

17. A handheld diabetes management device for classifying blood samples and identifying medically relevant patterns in groups of blood samples, the handheld diabetes management device comprising:
a blood glucose (bG) measurement engine that measures bG levels in blood samples input to the handheld diabetes management device via bG test strips;
a display;
a clock tracking a present date and time;
a processor; and
memory including code executed by the processor for:
storing the bG level and a time of receipt of the blood sample in memory;
determining a classification of the blood sample based on a time of receipt of the blood sample;
storing the classification of the blood sample in the memory, wherein the classification is one of a fasting sample, a pre-breakfast sample, a post-breakfast sample, a pre-lunch sample, a post-lunch sample, a pre-dinner sample, a post-dinner sample, and a bed time sample;
in response to the receipt of the blood sample, selecting a group of stored bG levels having the classification of the blood sample and that were received within a predetermined period before receipt of the blood sample;
calculating a bG evaluation parameter from the selected bG levels;
evaluating the bG evaluation parameter in relation to first predetermined criteria, the first predetermined criteria including a first threshold indicative of a high bG level or a low bG level;
selectively displaying, on the display, an indication of recognition of a pattern in the selected bG levels when the bG evaluation parameter is greater than or less than the first threshold; and
removing the indication from the display only in response to receipt of predetermined user input indicative of an acknowledgement of the presence of the pattern.

18. The handheld diabetes management device of claim 17 wherein the memory further includes code for storing the classification for the blood sample based on user input indicative of the classification.

19. The handheld diabetes management device of claim 17 wherein the memory further includes code for;
displaying the bG level of the blood sample; and,
before displaying the bG level, determining the classification of the blood sample.

20. The handheld diabetes management device of claim 17 wherein the memory further includes code for, when reminder data associated with one of the classifications is enabled, displaying a reminder to provide a blood sample at a predetermined time associated with the one of the classifications.

21. The handheld diabetes management device of claim 20 wherein the memory further includes code for updating the reminder data based on user input indicative of whether to display reminders to provide a blood sample at the predetermined time.

22. The handheld diabetes management device of claim 17 wherein the memory further includes code for:
determining a first daily event preceding a second daily event associated with the classification; and,
during a day following the receipt of the blood sample, displaying the indication of the pattern in the selected bG levels at a time associated with the first daily event.

23. A method for classifying blood samples and identifying medically relevant patterns in groups of blood samples, the method comprising:
measuring, by a blood glucose (bG) measurement engine of a handheld diabetes management device, a bG level in a blood sample received by the handheld diabetes management device via a bG test strip;
by a processor of the handheld diabetes management device, storing the bG level and a time of receipt of the blood sample in memory of the handheld diabetes management device;
by the processor, storing a classification of the blood sample in the memory, wherein the classification is one of a fasting sample, a pre-breakfast sample, a post-breakfast sample, a pre-lunch sample, a post-lunch sample, a pre-dinner sample, a post-dinner sample, and a bed time sample;
by the processor, selecting a group of stored bG levels having one of the classifications;
by the processor, generating an indicator of recognition of a pattern in the selected group of bG levels when a bG evaluation parameter calculated based on the selected bG levels is one of greater than a first threshold indicative of a high bG level and less than a second threshold indicative of a low bG level;
by the processor, in response to a user request to display recognized patterns in bG levels:
generating a list of recognized patterns including the pattern in the selected bG levels;
prioritizing the list based on predetermined prioritization criteria; and
displaying the list on a display of the handheld diabetes management device.

24. The method of claim 23 further comprising storing the classification based on user input indicative of the classification.

25. The method of claim 23 further comprising, when reminder data associated with one of the classifications is enabled, displaying a reminder to provide a blood sample at a predetermined time associated with the one of the classifications.

26. The method of claim 25 further comprising updating the reminder data based on user input indicative of whether to display reminders to provide a blood sample at the predetermined time.

27. The method of claim 23 further comprising determining the classification for the blood sample based on the time of receipt of the blood sample.

28. The method of claim 27 further comprising determining that the classification of the blood sample is a fasting sample when the time of receipt of the blood sample is within a predetermined time window around a predetermined time associated with fasting samples.

29. The method of claim 27 further comprising determining that the classification of the blood sample is a pre-breakfast sample when the time of receipt of the blood sample is within a predetermined time window around a predetermined time associated with breakfast.

30. The method of claim 29 further comprising determining that the classification of the blood sample is a post-breakfast sample when the time of receipt of the blood sample is within a predetermined period after a second time of receipt of a second blood sample classified as a pre-breakfast sample.

31. The method of claim 27 further comprising determining that the classification of the blood sample is a post-breakfast sample when the time of receipt of the blood sample is within a predetermined period after a second time of receipt of user input indicative of a start of breakfast.

32. The method of claim 27 further comprising determining that the classification of the blood sample is a pre-lunch sample when the time of receipt of the blood sample is within a predetermined time window around a predetermined time associated with lunch.

33. The method of claim 32 further comprising determining that the classification of the blood sample is a post-lunch sample when the time of receipt of the blood sample is within a predetermined period after a second time of receipt of a second blood sample classified as a pre-lunch sample.

34. The method of claim 27 further comprising determining that the classification of the blood sample is a post-lunch sample when the time of receipt of the blood sample is within a predetermined period after a second time of receipt of user input indicative of a start of lunch.

35. The method of claim 27 further comprising determining that the classification of the blood sample is a pre-dinner sample when the time of receipt of the blood sample is within a predetermined time window around a predetermined time associated with dinner.

36. The method of claim 35 further comprising determining that the classification of the blood sample is a post-dinner sample when the time of receipt of the blood sample is within a predetermined period after a second time of receipt of a second blood sample classified as a pre-dinner sample.

37. The method of claim 27 further comprising determining that the classification of the blood sample is a post-dinner sample when the time of receipt of the blood sample is within a predetermined period after a second time of receipt of user input indicative of a start of dinner.

38. The method of claim 27 further comprising determining that the classification of the blood sample is a bed time sample when a time stamp of the blood sample is within a predetermined time window around a predetermined time associated with bed time samples.

39. The method of claim 23 further comprising:
displaying the bG level of the blood sample; and,
before displaying the bG level, determining the classification of the blood sample.

40. The method of claim 23 further comprising:
determining a first daily event preceding a second daily event associated with the classification; and,
during a day following the receipt of the blood sample, displaying the indication of the pattern in the selected bG levels at a time associated with the first daily event.

41. A handheld diabetes management device for classifying blood samples and identifying medically relevant patterns in groups of blood samples, the handheld diabetes management device comprising:
a blood glucose (bG) measurement engine that measures bG levels in blood samples input to the handheld diabetes management device via bG test strips;
a display;

a clock tracking a present date and time;
a processor; and
memory including code executed by the processor for:
    measuring a blood glucose (bG) level in a blood sample received by the handheld diabetes management device;
    storing the bG level and a time of receipt of the blood sample in the memory;
    storing a classification of the blood sample in the memory, wherein the classification is one of a fasting sample, a pre-breakfast sample, a post-breakfast sample, a pre-lunch sample, a post-lunch sample, a pre-dinner sample, a post-dinner sample, and a bed time sample;
    selecting a group of stored bG levels having one of the classifications;
    generating an indicator of recognition of a pattern in the selected group of bG levels when a bG evaluation parameter calculated based on the selected bG levels is one of greater than a first threshold indicative of a high bG level and less than a second threshold indicative of a low bG level;
    in response to a user request to display recognized patterns in bG levels:
        generating a list of recognized patterns including the pattern in the selected bG levels;
        prioritizing the list based on predetermined prioritization criteria; and
        displaying the list on the display.

42. The handheld diabetes management device of claim 41 wherein the memory further includes code for determining the classification for the blood sample based on the time of receipt of the blood sample.

43. The handheld diabetes management device of claim 41 wherein the memory further includes code for storing the classification for the blood sample based on user input indicative of the classification.

44. The handheld diabetes management device of claim 41 wherein the memory further includes code for:
    displaying the bG level of the blood sample; and,
    before displaying the bG level, determining the classification of the blood sample.

45. The handheld diabetes management device of claim 41 wherein the memory further includes code for, when reminder data associated with one of the classifications is enabled, displaying a reminder to provide a blood sample at a predetermined time associated with the one of the classifications.

46. The handheld diabetes management device of claim 45 wherein the memory further includes code for updating the reminder data based on user input indicative of whether to display reminders to provide a blood sample at the predetermined time.

47. The handheld diabetes management device of claim 41 wherein the memory further includes code for:
    determining a first daily event preceding a second daily event associated with the classification; and,
    during a day following the receipt of the blood sample, displaying the indication of the pattern in the selected bG levels at a time associated with the first daily event.

48. A method for automatically classifying blood samples, the method comprising:
    measuring, by a blood glucose (bG) measurement engine of a handheld diabetes management device, a bG level in a blood sample received by the handheld diabetes management device via a bG test strip;
    storing, by a processor of the handheld diabetes management device, the bG level and a time of receipt of the blood sample in memory of the handheld diabetes management device;
    classifying, by the processor of the handheld diabetes management device, the blood sample as one of a fasting sample, a pre-breakfast sample, a post-breakfast sample, a pre-lunch sample, a post-lunch sample, a pre-dinner sample, a post-dinner sample, and a bed time sample, the classifying including:
        classifying the blood sample as a post-breakfast sample when the time of receipt of the blood sample is within a predetermined period of receipt of a blood sample classified as a pre-breakfast sample;
        classifying the blood sample as a post-lunch sample when the time of receipt of the blood sample is within a predetermined period of receipt of a blood sample classified as a pre-lunch sample;
        classifying the blood sample as a post-dinner sample when the time of receipt of the blood sample is within a predetermined period of receipt of a blood sample classified as a pre-dinner sample;
        classifying the blood sample as one of a pre-breakfast sample and a post-breakfast sample when the time of receipt of the blood sample is within a predetermined period of a predetermined time of day associated with a breakfast meal;
        classifying the blood sample as one of a pre-lunch sample and a post-lunch sample when the time of receipt of the blood sample is within a predetermined period of a predetermined time of day associated with a lunch meal; and
        classifying the blood sample as one of a pre-dinner sample and a post-dinner sample when the time of receipt of the blood sample is within a predetermined period of a predetermined time of day associated with a dinner meal; and
    storing, by the processor of the handheld diabetes management device, an indicator of the classification of the blood sample in the memory of the handheld diabetes management device; and
    by the processor, selectively displaying the bG level of the blood sample on a display of the handheld diabetes management device.

\* \* \* \* \*